United States Patent
Valcarce Lopez et al.

(10) Patent No.: US 10,456,406 B2
(45) Date of Patent: *Oct. 29, 2019

(54) USE OF A PPAR-δ AGONIST FOR REDUCING LOSS OF MUSCLE STRENGTH, MUSCLE MASS, OR TYPE I MUSCLE FIBERS IN AN IMMOBILIZED LIMB

(71) Applicant: vTv Therapeutics LLC, High Point, NC (US)

(72) Inventors: Maria Carmen Valcarce Lopez, Oak Ridge, NC (US); Eliot Ohlstein, Glenmoore, PA (US)

(73) Assignee: VTV THERAPEUTICS LLC, High Point, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/950,949

(22) Filed: Apr. 11, 2018

(65) Prior Publication Data

US 2018/0296562 A1    Oct. 18, 2018

Related U.S. Application Data

(63) Continuation of application No. 15/286,661, filed on Oct. 6, 2016, now Pat. No. 9,968,613, which is a continuation of application No. 14/478,594, filed on Sep. 5, 2014, now Pat. No. 9,487,493.

(60) Provisional application No. 61/896,343, filed on Oct. 28, 2013, provisional application No. 61/875,214, filed on Sep. 9, 2013.

(51) Int. Cl.
| | |
|---|---|
| *A61K 31/5375* | (2006.01) |
| *C07D 295/096* | (2006.01) |
| *A61K 31/192* | (2006.01) |
| *A61K 9/00* | (2006.01) |

(52) U.S. Cl.
CPC ........ *A61K 31/5375* (2013.01); *A61K 9/0053* (2013.01); *A61K 31/192* (2013.01); *C07D 295/096* (2013.01)

(58) Field of Classification Search
CPC .................................................. A61K 31/5375
See application file for complete search history.

(56) References Cited

U.S. PATENT DOCUMENTS

| | | | |
|---|---|---|---|
| 7,129,268 B2 | 10/2006 | Jeppesen et al. | |
| 7,943,613 B2 | 5/2011 | Sauerberg et al. | |
| 7,943,669 B2 | 5/2011 | Ebdrup | |
| 8,008,348 B2 | 8/2011 | Steiner et al. | |
| 8,217,086 B2 | 7/2012 | Ebdrup | |
| 8,362,016 B2 | 1/2013 | Sauerberg et al. | |
| 8,388,968 B2 | 3/2013 | Berger et al. | |
| 8,426,473 B2 | 4/2013 | Ebdrup | |
| 8,551,993 B2 | 10/2013 | Sauerberg et al. | |
| 9,487,493 B2* | 11/2016 | Valcarce Lopez | ......................... C07D 295/096 |
| 9,968,613 B2* | 5/2018 | Valcarce Lopez | ......................... C07D 295/096 |
| 2008/0187928 A1 | 8/2008 | Evans et al. | |
| 2011/0092517 A1* | 4/2011 | Barbaras | .............. A61K 31/381 514/254.02 |
| 2013/0203712 A1 | 8/2013 | Adams et al. | |
| 2014/0024645 A1 | 1/2014 | Sauerberg et al. | |
| 2017/0027950 A1 | 2/2017 | Valcarce Lopez et al. | |

FOREIGN PATENT DOCUMENTS

| | | |
|---|---|---|
| WO | WO-9727847 A1 | 8/1997 |
| WO | WO-9727857 A1 | 8/1997 |
| WO | WO-9728115 A1 | 8/1997 |
| WO | WO-9728137 A1 | 8/1997 |
| WO | WO-9728149 A1 | 8/1997 |
| WO | WO-9827974 A1 | 7/1998 |
| WO | WO-9904815 A1 | 2/1999 |
| WO | WO-0100603 A1 | 1/2001 |
| WO | WO-0125181 A1 | 4/2001 |
| WO | WO-0125226 A1 | 4/2001 |
| WO | WO-0134200 A1 | 5/2001 |
| WO | WO-0160807 A1 | 8/2001 |
| WO | WO-0179197 A1 | 10/2001 |
| WO | WO-0214291 A1 | 2/2002 |
| WO | WO-0228434 A2 | 4/2002 |
| WO | WO-0246154 A1 | 6/2002 |
| WO | WO-0250048 A1 | 6/2002 |
| WO | WO-02059098 A1 | 8/2002 |
| WO | WO-02062774 A1 | 8/2002 |
| WO | WO-02070011 A2 | 9/2002 |
| WO | WO-02076957 A1 | 10/2002 |
| WO | WO-03016291 A1 | 2/2003 |
| WO | WO-03024395 A2 | 3/2003 |
| WO | WO-03033493 A1 | 4/2003 |
| WO | WO-03035603 A1 | 5/2003 |
| WO | WO-03072100 A1 | 9/2003 |

(Continued)

OTHER PUBLICATIONS

Abadi et al. Limb immobilization induces a coordinate down-regulation of mitochondrial and other metabolic pathways in men and women. PLoS One 4(8):e6518 (2009).

(Continued)

*Primary Examiner* — Rei Tsang Shiao

(74) *Attorney, Agent, or Firm* — Wilson Sonsini Goodrich & Rosati

(57) ABSTRACT

The present invention provides methods for reducing loss of muscle strength, muscle mass, or Type I muscle fibers in an immobilized limb by administering (E)-[4-[3-(4-Fluorophenyl)-3-[4-[3-(morpholin-4-yl)propynyl]phenyl]allyloxy]-2-methyl-phenoxy]acetic acid or a pharmaceutically acceptable salt thereof.

11 Claims, 2 Drawing Sheets

(56) References Cited

FOREIGN PATENT DOCUMENTS

| | | |
|---|---|---|
| WO | WO-03074050 A1 | 9/2003 |
| WO | WO-03074051 A1 | 9/2003 |
| WO | WO-03074052 A1 | 9/2003 |
| WO | WO-03074495 A1 | 9/2003 |
| WO | WO-03084916 A2 | 10/2003 |
| WO | WO-03097607 A1 | 11/2003 |
| WO | WO-2004000315 A1 | 12/2003 |
| WO | WO-2004000762 A2 | 12/2003 |
| WO | WO-2004005253 A1 | 1/2004 |
| WO | WO-2004037776 A2 | 5/2004 |
| WO | WO-2004060871 A1 | 7/2004 |
| WO | WO-2004063165 A1 | 7/2004 |
| WO | WO-2004063166 A1 | 7/2004 |
| WO | WO-2004073606 A2 | 9/2004 |
| WO | WO-2004080943 A1 | 9/2004 |
| WO | WO-2004080947 A1 | 9/2004 |
| WO | WO-2004092117 A1 | 10/2004 |
| WO | WO-2004092130 A2 | 10/2004 |
| WO | WO-2004093879 A1 | 11/2004 |
| WO | WO-2005060958 A1 | 7/2005 |
| WO | WO-2005097098 A2 | 10/2005 |
| WO | WO-2005097762 A2 | 10/2005 |
| WO | WO-2005097763 A2 | 10/2005 |
| WO | WO-2005115383 A2 | 12/2005 |
| WO | WO-2006055187 A1 | 5/2006 |
| WO | WO-2007003581 A1 | 1/2007 |
| WO | WO2007/071766 * | 6/2007 |
| WO | WO-2007071766 A2 | 6/2007 |
| WO | WO-2015035171 A1 | 3/2015 |

OTHER PUBLICATIONS

Barbaras et al. CAS 154:276074 (2 pgs.) (2011).
Berge et al. Pharmaceutical Salts. Journal of Pharmaceutical Sciences 66(1):1-19 (Jan. 1977).
Bernardo et al. Postnatal PPAR-delta Activation and Myostatin Inhibition Exert Distinct yet Complimentary Effects on the Metabolic Profile of Obese Insulin-Resistant Mice. PLoS One 5(6):1-11 (2010).
Castillero et al. PPAR-beta/delta Regulates Glucocorticoid- and Sepsis-Induced FOXO1 Activation and Muscle Wasting. PLOS One 8(3)(e59726):1-16 (2013).
De Boer et al. The temporal responses of protein synthesis, gene expression and cell signalling in human quadriceps muscle and patellar tendon to disuse. J Physiol 585:241-251.
De Grey. Foreseeable pharmaceutical repair of age-related extracellular damage. Curr Drug Targets 7:1469-1477 (2006).
Ehrenborg et al. Regulation of Skeletal Muscle Physiology and Metabolism by Peroxisome Proliferator-Activated Receptor delta. Pharmacological Reviews 61(3):373-393 (2009).
Fedorova et al. Peroxisome Proliferator-Activated Receptor delta Agonist, HPP593, Prevents Renal Necrosis under Chronic Ischemia. PLOS One 8(5):1-13 (2013).
Ferrando et al. Prolonged bed rest decreases skeletal muscle and whole body protein synthesis. Am J Physiol 270:E627-633 (1996).
Fritz et al. Low-intensity exercise increases skeletal muscle protein expression of PPARdelta and UCP3 in type 2 diabetic patients. Diabetes Metab Res Rev 2:492-498 (2006).
Gaudel et al. Pharmacological activation of PPARbeta promotes rapid and calcineurin-dependent fiber remodeling and angiogenesis in mouse skeletal muscle. American Journal of Physiology 295(2):E297-E304 (2008).
Gibson et al. Decrease in human quadriceps muscle protein turnover consequent upon leg immobilization. Clin Sci (Lond) 72:503-509 (1987).
Handschin et al. Skeletal Muscle Fiber-type Switching, Exercise Intolerance, and Myopathy in PGC-1-alpha Muscle-specific Knockout Animals. The Journal of Biological Chemistry 282(41):30014-30021 (2007).

Herridge et al. Functional Disability 5 Years after Acute Respiratory Distress Syndrome. The New England Journal of Medicine, 364(14):1293-1304 (2011).
Hough et al. The role of future longitudinal studies in ICU survivors: understanding determinants and pathophysiology of weakness and neuromuscular dysfunction. Curr Opin Crit Care 13:489-496 (2007).
Hough. Improving physical function during and after critical care. Curr Opin Crit Care 19(5):488-495 (2013).
Jahnke et al. Metabolic remodeling agents show beneficial effects in the dystrophin-deficient mdx mouse model. Skeletal Muscle 2(16):1-11 (2012).
Johri et al. Pharmacologic activation of mitochondrial biogenesis exerts widespread beneficial effects in a transgenic mouse model of Huntington's disease. Human Molecular Genetics 21(5):1124-1137 (2012) Advance Access published on Nov. 17, 2011.
Mahoney et al. Analysis of global mRNA expression in human skeletal muscle during recovery from endurance exercise. FASEB J 19:1498-1500 (2005).
Miura et al. Pharmacological activation of PPAR-beta/delta stimulates utrophin A expression in skeletal muscle fibers and restores sarcolemmal integrity in mature mdx mice. Human Molecular Genetics 18(23):4640-4649 (2009) Advance Access published on Sep. 10, 2009.
Narkar et al. AMPK and PPAR-sigma agonists are exercise mimetics. Cell 134(3):405-415 (2008).
Russell et al. Endurance training in humans leads to fiber type-specific increases in levels of peroxisome proliferator-activated receptor-gamma coactivator-1 and peroxisome proliferator-activated receptor-alpha in skeletal muscle. Diabetes 52:2874-2881 (2003).
Sacheck et al. Rapid disuse and denervation atrophy involve transcriptional changes similar to those of muscle wasting during systemic diseases. The FASEB Journal 21:140-155 (2007).
Sadowski et al. GAL4 fusion vectors for expression in yeast or mammalian cells. Gene 118:137 (1992).
Sandri et al. PGC-1-alpha protects skeletal muscle from atrophy by suppressing Fox03 action and atrophy-specific gene transcription. PNAS 103(44):16260-16265 (2006).
Shangraw et al. Insulin responsiveness of protein metabolism in vivo following bedrest in humans. Am J Physiol 255:E548-558 (1988).
Tanaka et al. Activation of peroxisome proliferator-activated receptor delta induces fatty acid beta-oxidation in skeletal muscle and attenuates metabolic syndrome. PNAS USA 100:15924-15929 (2003).
Tesch et al. Skeletal muscle proteolysis in response to short-term unloading in humans. J Appl Physiol 105:902-906 (2008).
U.S. Appl. No. 14/478,594 Office Action dated Nov. 23, 2015.
U.S. Appl. No. 15/286,661 Office Action dated Jun. 5, 2017.
Wang et al. Peroxisome-proliferator-activated receptor delta activates fat metabolism to prevent obesity. Cell 113:159-170 (2003).
Wang et al. Regulation of Muscle Fiber Type and Running Endurance by PPAR-delta. PLoS Biol. 2:e294 (2004).
Watt et al. Suppression of plasma free fatty acids upregulates peroxisome proliferator-activated receptor (PPAR) alpha and delta and PPAR coactivator 1alpha in human skeletal muscle, but not lipid regulatory genes. J Mol Endocrinol 33:533-544 (2004).
Webster et al. Nucleotide sequence of the galactose gene cluster of Kluyveromyces lactis. Nucleic Acids Res. 16:8192-8194 (1988).
Wolfram. Effects of the PPAR delta agonist GW501516 on exercise performance of mice. FASEB J 21(5):A580 (Astract No. 615.26. Experimental Biology 2007 Annual Meeting; Washington, D.C. Apr. 28, 2007 to May 2, 2007.
Yasuda et al. Sex-based differences in skeletal muscle function and morphology with short-term limb immobilization. J Appl Physiol 99: 1085-1092 (2005).
Zingarelli et al. Peroxisome Proliferator-Activated Receptor delta Regulates Inflammation via NF-kappa-B Signaling in Polymicrobial Sepsis. The American Journal of Pathology 177(4):1834-1847 (2010).

* cited by examiner

# USE OF A PPAR-δ AGONIST FOR REDUCING LOSS OF MUSCLE STRENGTH, MUSCLE MASS, OR TYPE I MUSCLE FIBERS IN AN IMMOBILIZED LIMB

CROSS-REFERENCE

This application is a Continuation of U.S. application Ser. No. 15/286,661, filed Oct. 6, 2016, now U.S. Pat. No. 9,968,613, which is a continuation of U.S. application Ser. No. 14/478,594, now U.S. Pat. No. 9,487,493, filed Sep. 5, 2014, which claims the benefit of U.S. Provisional Application No. 61/896,343, filed Oct. 28, 2013, and U.S. Provisional Application No. 61/875,214, filed Sep. 9, 2013, all of which are hereby incorporated by reference in its entirety.

BACKGROUND OF THE INVENTION

Field of Invention

The invention relates to the fields of pharmacology and medicine, and provides therapeutic methods and compositions for treating muscle atrophy.

Description of Related Art

Muscle atrophy refers to the loss of muscle mass and/or to the progressive weakening and degeneration of muscles, including the skeletal or voluntary muscles (which control movement), cardiac muscles (which control the heart), and smooth muscles. Skeletal muscle atrophy is associated with bed rest, corticosteroid use, denervation, chronic renal failure, limb immobilization, neuromuscular disorders, sarcopenia of aging, and arthritis. Irrespective of the underlying cause of atrophy, reduced muscle activation/contractile activity (hypodynamia) is an invariant feature. The fundamental molecular mechanism(s) underlying muscle atrophy and numerous cellular processes include decreased protein synthesis, increased protein degradation, suppression of bioenergetic pathways associated with mitochondrial function, and increased oxidative stress (Abadi et al., PLoS ONE 4(8):e6518 (2009)).

Upstream triggers that initiate muscle atrophy are poorly understood and may vary depending on the pathological context; however, animal data suggests that disparate atrophic stimuli converge on the activation of protein degradation, particularly the ubiquitin (Ub)-26S proteasomal pathway. Two novel Ub-protein ligases, atrogin-1 (muscle atrophy F-box protein) and muscle ring finger protein (MuRF-1), are consistently up-regulated in murine models of muscle atrophy, and are thought to ubiquitinate both regulatory (e.g., calcineurin and MyoD) and structural (e.g., myosin and troponin I) proteins, thus directing the specific degradation of proteins during muscle atrophy (Abadi et al., PLoS ONE 4(8):e6518 (2009)).

While much progress has been made towards delineating the underlying functional alterations and signaling pathways that mediate muscle atrophy in animal models, few studies have examined muscle atrophy in humans. Early reports concerning protein turnover in humans demonstrated that mixed muscle protein synthesis rates decline during muscle atrophy while protein degradation rates appear unchanged (de Grey, Curr. Drug Targets 7:1469-1477 (2006); Ferrando et al., Am. J. Physiol. 270:E627-633 (1996); Gibson et al., Clin. Sci. (Lond) 72:503-509 (1987); Shangraw et al., Am. J. Physiol. 255:E548-558 (1988)). This was confirmed in a recent study in which the rate of myofibrillar protein synthesis decreased by 50% following 10 d of unilateral limb suspension (ULS) in human subjects (de Boer et al., J. Physiol. 585:241-251 (2007)). These studies have emphasized the suppression of protein synthesis during atrophy in human muscle, which contrasts with studies in murine models that point primarily towards increased protein degradation. However, one recent study found that myofibrillar protein degradation was increased in humans as early as 72 h following ULS (Tesch et al., J. Appl. Physiol. 105:902-906 (2008)). In addition, the expression of atrogin-1 and MuRF-1 during muscle atrophy in humans is contentious, with some studies showing increased atrogin-1 and MuRF-1 mRNA, but not others (Abadi et al., PLoS ONE 4(8):e6518 (2009)).

In a study conducted by Abadi and colleagues (Abadi et al., PLoS ONE 4(8):e6518 (2009)), the transcriptional suppression of bioenergetic and mitochondrial genes dominated the immobilization-induced transcription and was evident as early as 48 hours following immobilization. These transcriptional changes were accompanied by declines in both the protein level and enzymatic activity of several mitochondrial proteins following 14 days of immobilization. In addition, atrogin-1 and MuRF-1 mRNA was significantly up-regulated early during the progression of muscle atrophy, and protein ubiquitination was increased following 48 hours of immobilization, but not following 14 days of immobilization. Lastly, mTOR phosphorylation decreased significantly following 48 hours of immobilization, but not following 14 days of immobilization.

Existing treatments for muscle atrophy include exercise or physical therapy (when possible), functional electrical stimulation of muscles, and amino acid therapy (e.g., administration of branched-chain amino acids (BAAs)) to attempt to regenerate damaged or atrophied muscle tissue. In severe cases of muscle atrophy, anabolic steroids such as methandrostenolone have been administered to patients. However, the efficacy of existing treatments has been limited, and the use of BAAs and anabolic steroids are both known to produce side effects. For example, BAAs can cause fatigue and loss of coordination, while anabolic steroids can cause cardiovascular disease, impaired liver function, and both estrogenic and androgenic effects (e.g., acne, body/facial hair growth, male pattern baldness, and gynecomastia). Accordingly, there remains a need for improved therapies for the treatment of muscle atrophy.

The present invention relates to the use of a PPARδ agonist to treat muscle atrophy in a subject in need thereof.

BRIEF SUMMARY OF THE INVENTION

Certain variations of the present invention provide improved treatment of muscle atrophy by administering a PPARδ agonist to a subject in need thereof.

The present invention is directed to a method of treating disuse-associated muscle atrophy in a subject in need thereof comprising administering to the subject an effective amount of a PPARδ agonist. In one embodiment, the PPARδ agonist is selected from the group consisting of:
 (Z)-[2-Methyl-4-[3-(4-methylphenyl)-3-[4-[3-(morpholin-4-yl)propynyl]phenyl]allyloxy]-phenoxy]acetic acid;
 (E)-[2-Methyl-4-[3-[4-[3-(pyrazol-1-yl)prop-1-ynyl]phenyl]-3-(4-trifluoromethylphenyl)-allyloxy]phenoxy]acetic acid;
 (E)-[4-[3-(4-Fluorophenyl)-3-[4-[3-(morpholin-4-yl)propynyl]phenyl]allyloxy]-2-methyl-phenoxy]acetic acid;

(E)-[2-Methyl-4-[3-[4-[3-(morpholin-4-yl)propynyl]phenyl]-3-(4-trifluoromethylphenyl)allyloxy]-phenoxy]acetic acid;

(E)-[4-[3-(4-Chlorophenyl)-3-[4-[3-(morpholin-4-yl)propynyl]phenyl]allyloxy]-2-methyl-phenoxy]acetic acid;

(E)-[4-[3-(4-Chlorophenyl)-3-[4-[3-(morpholin-4-yl)propynyl]phenyl]allyloxy]-2-methylphenyl]-propionic acid;

{4-[3-Isobutoxy-5-(3-morpholin-4-yl-prop-1-ynyl)-benzylsulfanyl]-2-methyl-phenoxy}-acetic acid;

{4-[3-Isobutoxy-5-(3-morpholin-4-yl-prop-1-ynyl)-phenylsulfanyl]-2-methyl-phenoxy}-acetic acid; and {4-[3,3-Bis-(4-bromo-phenyl)-allyloxy]-2-methyl-phenoxy}-acetic acid;

or a pharmaceutically acceptable salt thereof.

In a particular embodiment, the PPARδ agonist is (E)-[4-[3-(4-Fluorophenyl)-3-[4-[3-(morpholin-4-yl)propynyl]phenyl]allyloxy]-2-methyl-phenoxy]acetic acid or a pharmaceutically acceptable salt thereof.

In one embodiment, the present invention is directed to a method for reducing disuse-associated muscle atrophy in a subject in need thereof comprising administering to the subject an effective amount of a PPARδ agonist. In a particular embodiment, the disuse-associated muscle atrophy is caused by limb immobilization in the subject. In another particular embodiment, the disuse-associated muscle atrophy is caused by use of a mechanical ventilator by the subject.

In one embodiment, reducing disuse-associated muscle atrophy comprises reducing the rate of loss of muscle strength in a muscle tissue of the subject relative to a control, wherein the rate of loss of muscle strength comprises a comparison of one or more measurements of muscle strength in the subject to a baseline measurement of muscle strength in the same subject prior to a period of disuse, wherein muscle strength is measured by a muscle strength test. In another embodiment, reducing the rate of loss of muscle strength in the subject comprises a return to the subject's baseline measurement of muscle strength faster than the control following a period of disuse. In another embodiment, the loss of muscle strength in the subject is less than the loss of muscle strength relative to the control during a period of disuse.

In another embodiment, reducing disuse-associated muscle atrophy comprises reducing the rate of loss of muscle mass in a muscle tissue of the subject relative to a control, wherein the rate of loss of muscle mass comprises a comparison of one or more measurements of muscle volume in the subject to a baseline measurement of muscle volume in the same subject prior to a period of disuse, wherein muscle volume is measured by the cross-section area of a muscle. In another embodiment, reducing the rate of loss of muscle mass in the subject comprises a return to the subject's baseline measurement of muscle mass faster than the control following a period of disuse. In another embodiment, the loss of muscle mass in the subject is less than the loss of muscle mass relative to the control during a period of disuse.

In another embodiment, reducing disuse-associated muscle atrophy comprises reducing the rate of loss of Type I muscle fibers in a muscle tissue of the subject relative to a control, wherein the rate of loss of Type I muscle fibers comprises a comparison of one or more measurements of Type I muscle fibers in the subject to a baseline measurement of Type I muscle fibers in the same subject. In an embodiment, the amount of Type I muscle fibers is measured by using myosin ATPase staining of muscle samples. In another embodiment, reducing the rate of loss of Type I muscle fibers in the subject comprises a return to the subject's baseline measurement of Type I muscle fibers faster than the control following a period of disuse. In another embodiment, the loss of Type I muscle fibers in the subject is less than the loss of Type I muscle fibers relative to the control during a period of disuse.

In another embodiment, reducing disuse-associated muscle atrophy comprises reducing the rate of decrease in mitochondrial biogenesis in a muscle tissue of the subject relative to a control, wherein the rate of decrease in mitochondrial biogenesis comprises a comparison of one or more measurements of mitochondrial biogenesis in the subject to a baseline measurement of mitochondrial biogenesis in the same subject. In another embodiment, reducing the rate of decrease in mitochondrial biogenesis in the subject comprises a return to the subject's baseline measurement of mitochondrial biogenesis faster than the control following a period of disuse. In another embodiment, the decrease in mitochondrial biogenesis in the subject is less than the decrease in mitochondrial biogenesis relative to the control during a period of disuse.

In another embodiment, the methods of the present invention for reducing disuse-associated muscle atrophy comprise administration of a PPARδ agonist to a subject in need thereof before, during, or after a period of disuse, or any combination thereof.

This Summary is provided merely to introduce certain concepts, and is not intended to identify any key or essential features of the claimed subject matter.

DETAILED DESCRIPTION

Figure 1:
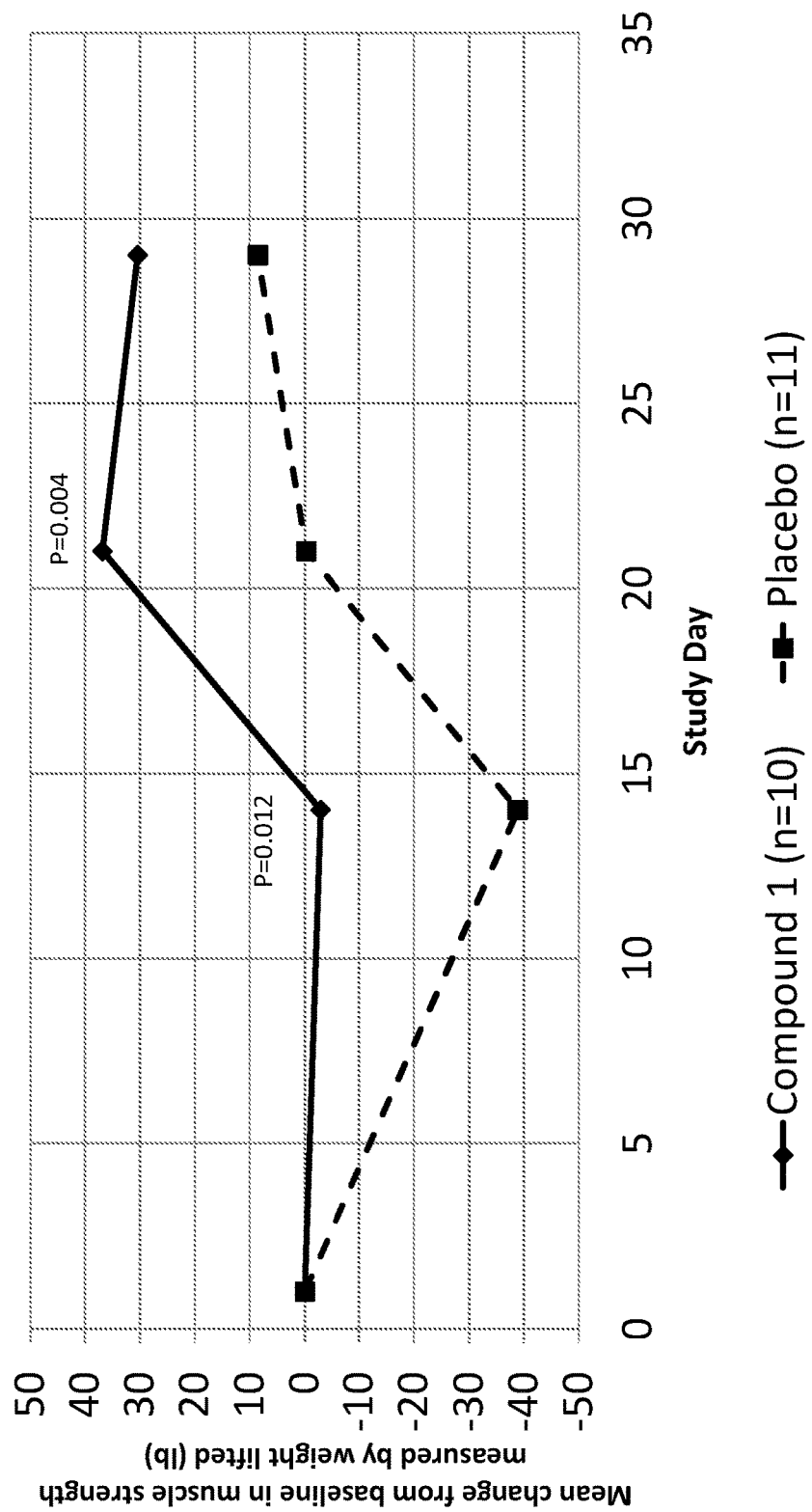
FIG. 1 shows a graph of mean changes from baseline in muscle strength representing the effect of administration of a PPARδ agonist on performance of a repeated measures knee extension strength test during (day 0 to day 14) and after (day 14 to day 21 and day 21 to day 29) limb immobilization in human subjects. Data reflects multiple imputation for missing and invalid data.

As used herein, the PPARδ agonist compounds of the present invention are useful in treating muscle atrophy in a subject in need thereof.

PPARδ is the most abundant PPAR isoform in skeletal muscle and has a higher expression in oxidative type I muscle fibers compared with glycolytic type II muscle fibers (Wang et al., PLoS Biol. 2:e294 (2004)). Both short-term exercise and endurance training lead to increased PPARδ expression in human and rodent skeletal muscle (Watt et al., J. Mol. Endocrinol. 33:533-544 (2004); Mahoney et al., FASEB J. 19:1498-1500 (2005); Russell et al., Diabetes 52:2874-2881 (2003); and Fritz et al., Diabetes Metab. Res. Rev. 2:492-498 (2006)). Rodent studies suggest that a key feature of PPARδ activation is induction of skeletal muscle fatty acid oxidation (Tanaka et al., Proc. Natl. Acad. Sci. U.S.A. 100:15924-15929 (2003); Wang et al., Cell 113:159-170 (2003)). On activation of PPARδ in skeletal muscle in mice, the fiber composition changes toward the oxidative type I with induction of fatty acid oxidation, mitochondrial respiration, oxidative metabolism, and slow-twitch contractile apparatus. In addition to the metabolic effects, this study also demonstrated that PPARδ stimulated peroxisome proliferator-activated receptor gamma coactivator-1 alpha (PGC-1α), an effect accompanied by mitochondrial biogenesis (Tanaka et al., Proc. Natl. Acad. Sci. U.S.A. 100:15924-15929 (2003)). Interestingly, this type of adaptation is identical to that seen in response to physical exercise, and indeed, mice with transgenic (Tg) overexpression of PPARδ exhibit increased running endurance (Wang et al., PLoS Biol. 2:e294 (2004)).

Methods of Treatment

The present invention is generally directed to methods of treating muscle atrophy in a subject in need thereof comprising administering to the subject an effective amount of a PPARδ agonist.

A muscle is a soft tissue found in most animals comprising muscle cells. Muscle cells contain protein filaments that can slide past one another and produce a contraction that changes both the length and shape of the muscle cell. Muscles function to produce force and motion. There are three types of muscles in the body: a) skeletal muscle (the muscle responsible for moving extremities and external areas of the bodies); b) cardiac muscle (the heart muscle); and c) smooth muscle (the muscle that is in the walls of arteries and bowel).

The term "muscle cell" as used herein refers to any cell that contributes to muscle tissue. Myoblasts, satellite cells, myotubes, and myofibril tissues are all included in the term "muscle cells" and may all be treated using the methods of the invention. Muscle cell effects may be induced within skeletal, cardiac, and smooth muscles.

Skeletal muscle, or voluntary muscle, is generally anchored by tendons to bone and is generally used to effect skeletal movement such as locomotion or in maintaining posture. Although some control of skeletal muscle is generally maintained as an unconscious reflex (e.g., postural muscles or the diaphragm), skeletal muscles react to conscious control. Smooth muscle, or involuntary muscle, is found within the walls of organs and structures such as the esophagus, stomach, intestines, uterus, urethra, and blood vessels. Unlike skeletal muscle, smooth muscle is not under conscious control. Cardiac muscle is also an involuntary muscle but more closely resembles skeletal muscle in structure and is found only in the heart. Cardiac and skeletal muscles are striated in that they contain sarcomeres that are packed into highly regular arrangements of bundles. By contrast, the myofibrils of smooth muscle cells are not arranged in sarcomeres and therefore are not striated.

Skeletal muscle is further divided into two broad types: Type I (or "slow twitch") and Type II (or "fast twitch"). Type I muscle fibers are dense with capillaries and are rich in mitochondria and myoglobin, which gives Type I muscle tissue a characteristic red color. Type I muscle fibers can carry more oxygen and sustain aerobic activity using fats or carbohydrates for fuel. Type I muscle fibers contract for long periods of time but with little force. Type II muscle fibers may be subdivided into three major subtypes (IIa, IIx, and IIb) that vary in both contractile speed and force generated. Type II muscle fibers contract quickly and powerfully but fatigue very rapidly, and therefore produce only short, anaerobic bursts of activity before muscle contraction becomes painful.

"Muscle atrophy" as used herein refers to a loss of muscle mass and/or to a progressive weakening and degeneration of muscles. The loss of muscle mass and/or the progressive weakening and degeneration of muscles can occur because of an unusually high rate of protein degradation, an unusually low rate of protein synthesis, or a combination of both. An unusually high rate of muscle protein degradation can occur due to muscle protein catabolism (i.e., the breakdown of muscle protein in order to use amino acids as substrates for gluconeogenesis).

In another embodiment, muscle atrophy refers to significant loss in muscle strength. By significant loss in muscle strength is meant a reduction of strength in diseased, injured, or unused muscle tissue in a subject relative to the same muscle tissue in a control subject. In an embodiment, a significant loss in muscle strength may be a reduction in strength of at least 10%, at least 15%, at least 20%, at least 25%, at least 30%, at least 35%, at least 40%, at least 45%, at least 50%, or more relative to the same muscle tissue in a control subject. In another embodiment, by significant loss in muscle strength is meant a reduction of strength in unused muscle tissue relative to the muscle strength of the same muscle tissue in the same subject prior to a period of nonuse. In an embodiment, a significant loss in muscle strength may be a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse. Muscle strength may be measured by a muscle strength test (see, e.g., Muscle Strength Test methods as described in the Examples below).

In another embodiment, muscle atrophy refers to significant loss in muscle mass. By significant loss in muscle mass is meant a reduction of muscle volume in diseased, injured, or unused muscle tissue in a subject relative to the same muscle tissue in a control subject. In an embodiment, a significant loss of muscle volume may be at least 10%, at least 15%, at least 20%, at least 25%, at least 30%, at least 35%, at least 40%, at least 45%, at least 50%, or more relative to the same muscle tissue in a control subject. In another embodiment, by significant loss in muscle mass is meant a reduction of muscle volume in unused muscle tissue relative to the muscle volume of the same muscle tissue in the same subject prior to a period of nonuse. In an embodiment, a significant loss in muscle tissue may be at least 10%, at least 15%, at least 20%, at least 25%, at least 30%, at least 35%, at least 40%, at least 45%, at least 50%, or more relative to the muscle volume of the same muscle tissue in the same subject prior to a period of nonuse. Muscle volume may be measured by evaluating the cross-section area of a muscle such as by Magnetic Resonance Imaging (MRI; see, e.g., muscle volume/cross-section area (CSA) MRI methods as described in the Examples below).

Among the general population, most muscle atrophy results from disuse. Disuse-associated muscle atrophy can result when a limb is immobilized (e.g., due to a limb or joint fracture or an orthopedic surgery such as a hip or knee replacement surgery). As used herein, "immobilization" or "immobilized" refers to the partial or complete restriction of movement of limbs, muscles, bones, tendons, joints, or any other body parts for an extended period of time (e.g., for 2 days, 3 days, 4 days, 5 days, 6 days, a week, two weeks, or more). A period of immobilization may include short periods or instances of unrestrained movement, such as to bathe, to replace an external device, or to adjust an external device. Limb immobilization may be carried out by any variety of external devices including, but not limited to, braces, slings, casts, bandages, and splints (any of which may be composed of hard or soft material including but not limited to cloth, gauze, fiberglass, plastic, plaster, or metal), as well as any variety of internal devices including surgically implanted splints, plates, braces, and the like. In the context of limb immobilization, the restriction of movement may involve a single joint or multiple joints (e.g., simple joints such as the shoulder joint or hip joint, compound joints such as the radiocarpal joint, and complex joints such as the knee joint, including but not limited to one or more of the following: articulations of the hand, shoulder joints, elbow joints, wrist joints, auxiliary articulations, sternoclavicular joints, vertebral articulations, temporomandibular joints, sacroiliac joints, hip joints, knee joints, and articulations of the foot), a single tendon or ligament or multiple tendons or ligaments (e.g., including but not limited to one or more of the following: the anterior cruciate ligament, the posterior cruciate ligament, rotator cuff tendons, medial collateral ligaments of the elbow and knee, flexor tendons of the hand, lateral ligaments of the ankle, and tendons and ligaments of the jaw or temporomandibular joint), a single bone or multiple bones (e.g., including but not limited to one or more of the following: the skull, mandible, clavicle, ribs, radius, ulna, humerous, pelvis, sacrum, femur, patella, phalanges, carpals, metacarpals, tarsals, metatarsals, fibula, tibia, scapula, and vertabrae), a single muscle or multiple muscles (e.g., including but not limited to one or more of the following: latissimus dorsi, trapezius, deltoid, pectorals, biceps, triceps, external obliques, abdominals, gluteus maximus, hamstrings, quadriceps, gastrocnemius, and diaphragm); a single limb or multiple limbs (e.g., one or more of the arms and legs), or the entire skeletal muscle system or portions thereof (e.g., in the case of a full body cast or spica cast).

Disuse-associated muscle atrophy can also result when the use of a limb is reduced (e.g., due to joint pain associated with rheumatoid arthritis or injury), or due to a prolonged period of inactivity due to illness, bed rest, or a debilitative state.

Disuse-associated muscle atrophy can also result from the use of mechanical ventilation by a subject. Even though mechanical ventilation is a life-saving measure for subjects with respiratory failure, complications associated with weaning patients from mechanical ventilation are common, in particular due to respiratory muscle weakness of the diaphragm, a skeletal muscle.

Accordingly, in one embodiment, the present invention is directed to a method for reducing disuse-associated muscle atrophy in a subject in need thereof comprising administering to the subject an effective amount of a PPARδ agonist. In a particular embodiment, the disuse-associated muscle atrophy is caused by limb immobilization in the subject. In another particular embodiment, the disuse-associated muscle atrophy is caused by use of a mechanical ventilator by the subject.

In one embodiment, reducing disuse-associated muscle atrophy comprises reducing the rate of loss of muscle strength in a muscle tissue of the subject relative to a control, wherein the rate of loss of muscle strength comprises a comparison of one or more measurements of muscle strength in the subject to a baseline measurement of muscle strength in the same subject, wherein muscle strength is measured by a muscle strength test (see, e.g., Muscle Strength Test methods as described in the Examples below). In another embodiment, reducing the rate of loss of muscle strength in the subject comprises a return to the subject's baseline measurement of muscle strength faster than the control following a period of disuse. In a further embodiment, reducing the rate of loss of muscle strength in the subject comprises a return to the subject's baseline measurement of muscle strength following a period of disuse in less than 95%, or less than 90%, or less than 85%, or less than 80%, or less than 75%, or less than 70%, or less than 65%, or less than 60%, or less than 55%, or less than 50% of the time to return to baseline for a control. In another embodiment, the loss of muscle strength in the subject is less than the loss of muscle strength relative to the control. In a further embodiment, the loss of muscle strength in the subject comprises less than a 50%, less than a 45%, less than a 40%, less than a 35%, less than a 30%, less than a 25%, less than a 20%, less than a 15%, less than a 10%, less than a 9%, less than an 8%, less than a 7%, less than a 6%, less than a 5%, less than a 4%, less than a 3%, less than a 2%, less than a 1%, or a 0% loss of muscle strength relative to the subject's baseline measurement of muscle strength prior to a period of disuse.

In another embodiment, reducing disuse-associated muscle atrophy comprises reducing the rate of loss of muscle mass in a muscle tissue of the subject relative to a control, wherein the rate of loss of muscle mass comprises a comparison of one or more measurements of muscle volume in the subject to a baseline measurement of muscle volume in the same subject, wherein muscle volume is measured by the cross-section area of a muscle (such as by Magnetic Resonance Imaging [MRI]; see, e.g., muscle volume/cross-section area [CSA] MRI methods as described in the Examples below). In another embodiment, reducing the rate of loss of muscle mass in the subject comprises a return to the subject's baseline measurement of muscle mass faster than the control. In a further embodiment, reducing the rate of loss of muscle mass in the subject comprises a return to the subject's baseline measurement of muscle mass following a period of disuse in less than 95%, or less than 90%, or less than 85%, or less than 80%, or less than 75%, or less than 70%, or less than 65%, or less than 60%, or less than 55%, or less than 50% of the time to return to baseline for a control. In another embodiment, the loss of muscle mass in the subject is less than the loss of muscle mass relative to the control. In a further embodiment, the loss of muscle mass in the subject comprises less than a 50%, less than a 45%, less than a 40%, less than a 35%, less than a 30%, less than a 25%, less than a 20%, less than a 15%, less than a 10%, less than a 9%, less than an 8%, less than a 7%, less than a 6%, less than a 5%, less than a 4%, less than a 3%, less than a 2%, less than a 1%, or a 0% loss of muscle mass relative to the subject's baseline measurement of muscle mass prior to a period of disuse.

In another embodiment, reducing disuse-associated muscle atrophy comprises reducing the rate of loss of Type I muscle fibers in a muscle tissue of the subject relative to a control, wherein the rate of loss of Type I muscle fibers comprises a comparison of one or more measurements of Type I muscle fibers in the subject to a baseline measurement of Type I muscle fibers in the same subject, wherein Type I muscle fibers is measured by using myosin ATPase staining. In another embodiment, reducing the rate of loss of Type I muscle fibers in the subject comprises a return to the subject's baseline measurement of Type I muscle fibers faster than the control. In a further embodiment, reducing the rate of loss of Type I muscle fibers in the subject comprises a return to the subject's baseline measurement of Type I muscle fibers following a period of disuse in less than 95%, or less than 90%, or less than 85%, or less than 80%, or less than 75%, or less than 70%, or less than 65%, or less than 60%, or less than 55%, or less than 50% of the time to return to baseline for a control. In another embodiment, the loss of Type I muscle fibers in the subject is less than the loss of Type I muscle fibers relative to the control. In a further embodiment, the loss of Type I muscle fibers in the subject comprises less than a 50%, less than a 45%, less than a 40%, less than a 35%, less than a 30%, less than a 25%, less than a 20%, less than a 15%, less than a 10%, less than a 9%, less than an 8%, less than a 7%, less than a 6%, less than a 5%, less than a 4%, less than a 3%, less than a 2%, less than a 1%, or a 0% loss of Type I muscle fibers relative to the subject's baseline measurement of Type I muscle fibers prior to a period of disuse.

Procedures for measuring Type I muscle fibers are described in N. Yasuda et al. J Appl Physiol 99: 1085-1092 (2005). For example, muscle specimens may be dissected of visible fat and connective tissue and placed into optimum cutting temperature embedding medium (OCT Tissue-Tek) with the orientation of the fibers perpendicular to the horizontal plane. The samples may be quickly frozen in isopentane, cooled by liquid nitrogen, and stored at −80 OC until subsequent histochemical analysis. At histochemical analysis, the OCT-mounted muscle samples may be serially sectioned to 10-μm thickness, and Type I, IIa, and IIx muscle fibers may be determined by using myosin ATPase staining.

In another embodiment, reducing disuse-associated muscle atrophy comprises reducing the rate of decrease in mitochondrial biogenesis in a muscle tissue of the subject relative to a control, wherein the rate of decrease in mitochondrial biogenesis comprises a comparison of one or more measurements of mitochondrial biogenesis in the subject to a baseline measurement of mitochondrial biogenesis in the same subject. In another embodiment, reducing the rate of decrease in mitochondrial biogenesis in the subject comprises a return to the subject's baseline measurement of mitochondrial biogenesis faster than the control. In a further embodiment, reducing the rate of decrease in mitochondrial biogenesis in the subject comprises a return to the subject's baseline measurement of mitochondrial biogenesis following a period of disuse in less than 95%, or less than 90%, or less than 85%, or less than 80%, or less than 75%, or less than 70%, or less than 65%, or less than 60%, or less than 55%, or less than 50% of the time to return to baseline for a control. In another embodiment, the decrease in mitochondrial biogenesis in the subject is less than the decrease in mitochondrial biogenesis relative to the control. In a further embodiment, the decrease in mitochondrial biogenesis in the subject comprises less than a 50%, less than a 45%, less than a 40%, less than a 35%, less than a 30%, less than a 25%, less than a 20%, less than a 15%, less than a 10%, less than a 9%, less than an 8%, less than a 7%, less than a 6%, less than a 5%, less than a 4%, less than a 3%, less than a 2%, less than a 1%, or a 0% decrease in mitochondrial biogenesis relative to the subject's baseline measurement of mitochondrial biogenesis prior to a period of disuse.

Mitochondrial biogenesis is measured by mitochondrial mass and volume through histological section staining using a fluorescently labeled antibody specific to the oxidative-phosphorylation complexes, such as the Anti-OxPhox Complex Vd subunit antibody from Life Technologies or using mitochondrial specific dyes in live cell staining, such as the Mito-tracker probes from Life Technologies. Mitochondrial biogenesis can also be measured by monitoring the gene expression of one or more mitochondrial biogenesis related transcription factors such as PGC1a, NRF1, or NRF2 using a technique such as QPCR.

In another embodiment, the method of the invention comprises a method for treating muscle atrophy caused by time spent in a zero gravity, reduced gravity, or perceived zero gravity environment in a subject in need thereof comprising administering to the subject an effective amount of a PPARδ agonist.

Muscle atrophy can also be associated with disease. Disease-associated muscle atrophy is less common than disuse-associated muscle atrophy and can result from diseases that either affect the nerves that supply individual muscles (i.e., neurogenic atrophy) or from diseases intrinsic to muscle tissue (i.e., muscle disease). In neurogenic atrophy, the nerve supply to the muscle can be interrupted or compromised by compression, injury, or disease within the nerve cells, resulting in a temporary or permanent nerve deficit. Diseases within nerve cells that can interrupt or compromise nerve supply to muscles include, for example, multiple sclerosis, amyotrophic lateral sclerosis (ALS, or Lou Gehrig's disease), Guillain-Barre syndrome, stroke, and viral infection of nerve cells (e.g., poliomyelitis). Muscle diseases can be intrinsic to muscle tissue (e.g., muscular dystrophy, polymyositis, or myotonia) or can occur as a response to systemic illness (e.g., hypo- or hyperthyroidism, adrenal gland depletion, diabetes mellitus, or autoimmune diseases). Sarcopenia is a debilitating disease that afflicts the elderly and is characterized by loss of muscle mass and function with advanced age. Generalized muscle wasting (cachexia) can also occur as a secondary consequence of such diseases as advanced cancer, Acquired Immune Deficiency Syndrome (AIDS), chronic obstructive lung disease, congestive heart failure, cardiomyopathy, chronic liver disease, renal disease, emphysema, tuberculosis, osteomalacia, hormonal deficiency, anorexia nervosa, generalized malnutrition, and drug abuse (e.g., abuse of alcohol, opiates, or steroids).

In another embodiment, the present invention provides methods to inhibit muscle atrophy and/or to increase muscle mass by providing to a subject in need thereof an effective amount of PPARδ agonist compound, and pharmaceutical compositions comprising compounds used in the methods. In another embodiment, the present invention provides methods to modulate muscle growth, or to increase muscle strength, or to maintain muscle strength, or to reduce loss of muscle strength, or to induce skeletal muscle hypertrophy, or to enhance tissue growth in vitro or in vivo, or to enhance muscle formation, and pharmaceutical compositions comprising compounds used in these methods. In each of these methods and pharmaceutical compositions, a PPARδ agonist compound is administered or used.

In another embodiment, the present invention provides a kit comprising at least one PPARδ agonist compound and one or more of: (a) a protein supplement; (b) an anabolic agent; (c) a catabolic agent; (d) a dietary supplement; (e) at least one agent known to treat a disorder associated with muscle wasting; (f) instructions for treating a disorder associated with cholinergic activity; or (g) instructions for using the compound to increase muscle mass and/or muscular strength. The kits can also comprise compounds and/or products co-packaged, co-formulated, and/or co-delivered with other components. For example, a drug manufacturer, a drug reseller, a physician, a compounding shop, or a pharmacist can provide a kit comprising a PPARδ agonist compound and/or product and another component for delivery to a patient. It is contemplated that the disclosed kits can be used in connection with the disclosed methods of making, the disclosed methods of using, and/or the disclosed compositions.

In another embodiment, a PPARδ agonist compound may be used in the treatment of muscle disorders. The muscle disorder can be skeletal muscle atrophy secondary to malnutrition, muscle disuse (secondary to voluntary or involuntary bed rest), neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization, chronic disease (including cancer, congestive heart failure, chronic pulmonary disease, chronic renal failure, chronic liver disease, diabetes mellitus, Cushing syndrome, and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, periods of exposure to zero or low gravity, or age-related sarcopenia. Thus, provided is a method for treating or preventing muscle atrophy in a subject suffering from one of these disorders or subject to one of these conditions, comprising administering to a subject a PPARδ agonist compound in an effective amount.

In another embodiment, the present invention provides a method of treating acute respiratory distress syndrome (ARDS) in a subject comprising administering to a subject a PPARδ agonist compound in an effective amount. In a further embodiment, the subject is on a mechanical ventilator. In a further embodiment, the method comprises reduction in muscle atrophy in the diaphragm.

In another embodiment, the present invention provides a method of reducing the period to weaning from a mechanical ventilator comprising administering to a subject a PPARδ agonist compound in an effective amount. In an embodiment, the period to weaning is reduced by at least 1 hour, at least 2 hours, at least 3 hours, at least 4 hours, at least 8 hours, at least 16 hours, at least 24 hours, at least 32 hours, at least 40 hours, at least 48 hours, at least 56 hours, at least 64 hours, or at least 72 hours.

In another embodiment, the decision to wean from a mechanical ventilator is evaluated using a manual muscle test (MMT) score. An MMT proximal subscore (5 muscle groups) may be initially assessed (such as prior to administration of the PPARδ agonist) and every 3 (+1) days thereafter after the initial assessment until hospital discharge, including the day of discharge or the day before. During periods of mechanical ventilation, MMT may be scheduled during sedation holiday. The MMT total score (12 muscle groups) may be performed one day after an order has been written for discharge from the ICU and every 7 (+1) days thereafter until hospital discharge. The muscle groups that may be assessed are bilateral shoulder abduction, elbow flexion, wrist extension, hip flexion, knee extension, and foot dorsiflexion. In another embodiment, the muscle groups that may be assessed include any grouping of the following: Trapezius (shoulder elevators); Deltoid middle (shoulder abductors); Biceps brachii (elbow flexors); Wrist extensors; Wrist flexors; Iliopsoas (hip flexors); Quadriceps femoris (knee extensors); Ankle dorsiflexors; Neck flexors; Gluteus medius (hip abductors); Neck extensors; Gluteus maximus (hip extensors); Hamstrings (knee flexors); and Ankle plantar flexors; including any group of 12.

The subject may be positioned in either the sitting or supine position, depending on the patient's clinical situation. Strength in each muscle group will be scored according to the six point MRC system, in which a score of 0 is no contraction; 1 is a flicker of contraction; 2 is active movement with gravity eliminated; 3 is active movement against gravity; 4 is active movement against gravity and resistance; and 5 is normal power. Proximal muscle strength, an outcome measure, may be scored as the mean of the scores for bilateral shoulder abduction and bilateral hip flexion, and may be referred to as the MMT proximal subscore.

In another embodiment, the present invention provides a method of decreasing the rate of lowering a patient's MMT score (or subscore) wherein the subject is subject to mechanical ventilation, of maintaining a subject's MMT score (or subscore), or increasing a subject's MMT score (or subscore), where the patient is subject to mechanical ventilation, comprising administering to a subject a PPARδ agonist compound in an effective amount. In an embodiment, the subject's MMT subscore for bilateral shoulder abduction and bilateral hip flexion is 6 or greater before weaning from mechanical ventilation.

In another embodiment, the present invention provides a method of increasing the days free of mechanical ventilation for a subject on mechanical ventilation. In an embodiment, the number of days free is out of 28 days. In another embodiment, the present invention provides a method of increasing the number of hospital free days of a subject on mechanical ventilation. In an embodiment, the number of hospital free days is out of 28 days.

Also provided is a method for increasing muscle mass, comprising administering to a subject a PPARδ agonist compound in an amount effective to increase the subject's muscle mass. In an embodiment, the subject is a mammal. In a further embodiment, the mammal is a primate. In a still further embodiment, the mammal is a human. In another embodiment, the subject is a domesticated animal. In a further embodiment, the domesticated animal is poultry. In an even further embodiment, the poultry is selected from chicken, turkey, duck, and goose. In a still further embodiment, the domesticated animal is livestock. In a further embodiment, the livestock animal is selected from pig, cow, horse, goat, bison, and sheep.

In another embodiment, the present invention provides a method of enhancing tissue or cell growth in vitro, the method comprising administering to the tissue or cells a PPARδ agonist compound in an amount effective to enhance growth of the tissue or cells. In a further embodiment, the tissue comprises animal cells. In a still further embodiment, the animal cells are muscle cells. In a further embodiment, the muscle cells are myosatellite cells. In an even further embodiment, any of the foregoing tissues or cells may be grown on a scaffold, bead, or other support matrix. In a further embodiment, the present invention provides a tissue or cells grown in the presence of a PPARδ agonist compound. In another embodiment, the tissue or cells grown may be implanted in a subject from whom the tissue or cells were originally harvested. In another embodiment, the tissue or cells grown may be implanted in a subject different from the subject from whom the tissue or cells were originally harvested.

In another embodiment, the present invention provides a method of enhancing tissue growth in vivo, the method comprising administering a PPARδ agonist compound in an amount effective to enhance growth of a tissue or cells following implantation of the tissue or cells into the subject. In a further embodiment, the tissue comprises animal cells. In a still further embodiment, the animal cells are muscle cells. In a further embodiment, the muscle cells are myosatellite cells. In an even further embodiment, any of the foregoing cells may be grown on a scaffold, bead, or other support matrix prior to implantation. In a further embodiment, the tissue or cells are grown in the presence of a PPARδ agonist compound. In another embodiment, the tissue grown may be implanted in a subject from whom the tissue or cells were originally harvested. In another embodiment, the tissue grown may be implanted in a subject different from the subject from whom the tissue or cells were originally harvested.

In another embodiment, the present invention provides uses of a PPARδ agonist compound as pharmacological tools in the development and standardization of in vitro and in vivo test systems for the evaluation of the effects of modulators of muscle hypertrophy or inhibitors of muscle atrophy related activity in laboratory animals such as cats, dogs, rabbits, monkeys, rats, and mice, as part of the search for new therapeutic agents to increase muscle mass and/or inhibit muscle hypertrophy.

In any of the embodiments herein where a PPARδ agonist compound is administered to a subject, the compound may be administered systemically, such as by parenteral injection or by oral consumption, and may be used to promote muscle growth and reduce muscle atrophy in all muscles, including those of the limbs and the diaphragm. A PPARδ agonist compound may also be administered locally, such as by a topical route or localized injection, and may be used to promote local muscle growth, as can be required following a localized injury or surgery.

In any of the embodiments herein where a PPARδ agonist compound is administered to a subject, the administration may be combined with a regime of physical therapy to inhibit muscle atrophy, or to increase muscle mass, or to inhibit loss of muscle strength, or to increase muscle strength, or to enhance muscle formation.

Accordingly, in an embodiment, the method of the invention comprises a method for treating a disease associated with muscle atrophy in a subject in need thereof comprising administering to the subject an effective amount of a PPARδ agonist.

Muscle atrophy can also be associated with injury. Injury-associated muscle atrophy can occur, for example, with severe burns and trauma, including, but not limited to, damage to the central nervous system (CNS) or peripheral nervous system (PNS), or exposure to toxic chemicals.

Accordingly, in an embodiment, the method of the invention comprises a method for treating injury-associated muscle atrophy in a subject in need thereof comprising administering to the subject an effective amount of a PPARδ agonist.

As used herein, "administer" or "administering" means to introduce, such as to introduce to a subject a compound(s) or composition. The term is not limited to any specific mode of delivery, and can include, but is not limited to, transdermal and oral delivery.

As used herein, "treat" or "treating" or "treatment" can refer to one or more of: delaying the progress of a disorder; controlling a disorder; delaying the onset of a disorder; ameliorating one or more symptoms characteristic of a disorder; or delaying the recurrence of a disorder, or characteristic symptoms thereof, depending on the nature of the disorder and its characteristic symptoms.

In some aspects of the invention, muscle atrophy may be predicted in a subject, for example, in the context of muscle atrophy caused by limb immobilization or caused by use of a mechanical ventilator by a subject. In such cases, treatment may be initiated prior to the condition predicted to cause muscle atrophy. For example, treatment of a subject with an effective amount of a PPARδ agonist may be initiated immediately before the condition predicted to cause muscle atrophy (e.g, immediately before limb immobilization or use of a mechanical ventilator). In another embodiment, treatment of a subject with an effective amount of a PPARδ agonist may be initiated at least 1 hour, at least 2 hours, at least 3 hours, at least 4 hours, at least 8 hours, at least 16 hours, at least 24 hours, at least 32 hours, at least 40 hours, at least 48 hours, at least 56 hours, at least 64 hours, or at least 72 hours before the condition predicted to cause muscle atrophy (e.g., immediately before limb immobilization or use of a mechanical ventilator).

Accordingly, in one embodiment the methods of the present invention for reducing disuse-associated muscle atrophy comprise administration of a PPARδ agonist to a subject in need thereof during a period of disuse. In another embodiment, the methods of the present invention for reducing disuse-associated muscle atrophy comprise administration of a PPARδ agonist to a subject in need thereof before a period of disuse. In another embodiment, the methods of the present invention for reducing disuse-associated muscle atrophy comprise administration of a PPARδ agonist to a subject in need thereof after a period of disuse. In another embodiment, the methods of the present invention for reducing disuse-associated muscle atrophy comprise administration of a PPARδ agonist to a subject in need thereof before, during, or after a period of disuse, or any combination thereof.

In treating muscle atrophy, diagnosing and assessing the severity of the condition and/or effectiveness of prevention or treatment is ultimately left to the subject and/or attending physician. However, a number of tools are available for assessing the severity of the condition and/or effectiveness of prevention or treatment, as described elsewhere herein.

As used herein, "subject" generally refers to a human, but also may include other mammals such as horses, cows, sheep, pigs, mice, rats, dogs, cats, and primates. In an embodiment, the subject is a human. In another embodiment, the subject is a mammal who exhibits one or more symptoms characteristic of a disorder. In another embodiment, the subject is a human who exhibits one or more symptoms characteristic of a disorder. The term subject does not require one to have any particular status or relationship with respect to a hospital, clinic, research facility, or physician (e.g., as an admitted patient, a study participant, or the like).

Dosages of the compounds used in the present invention must ultimately be set by an attending physician. General outlines of the dosages are provided herein below. Generally, a suitable dose of a PPARδ agonist, or a pharmaceutically acceptable salt thereof, for administration to a human will be in the range of about 0.1 mg/kg per day to about 25 mg/kg per day (e.g., about 0.2 mg/kg per day, about 0.3 mg/kg per day, about 0.4 mg/kg per day, about 0.5 mg/kg per day, about 0.6 mg/kg per day, about 0.7 mg/kg per day, about 0.8 mg/kg per day, about 0.9 mg/kg per day, about 1 mg/kg per day, about 2 mg/kg per day, about 3 mg/kg per day, about 4 mg/kg per day, about 5 mg/kg per day, about 6 mg/kg per day, about 7 mg/kg per day, about 8 mg/kg per day, about 9 mg/kg per day, about 10 mg/kg per day, about 15 mg/kg per day, about 20 mg/kg per day, or about 25 mg/kg per day). Alternatively, a suitable dose of a PPARδ agonist, or a pharmaceutically acceptable salt thereof, for administration to a human will be in the range of from about 0.1 mg/day to about 1000 mg/day; from about 1 mg/day to about 400 mg/day; or from about 1 mg/day to about 300 mg/day. In other embodiments, a suitable dose of a PPARδ agonist, or a pharmaceutically acceptable salt thereof, for administration to a human will be about 1 mg/day, about 2 mg/day, about 3 mg/day, about 4 mg/day, about 5 mg/day, about 6 mg/day, about 7 mg/day, about 8 mg/day, about 9 mg/day, about 10 mg/day, about 15 mg/day, about 20 mg/day, about 25 mg/day, about 30 mg/day, about 35 mg/day, about 40 mg/day, about 45 mg/day, about 50 mg/day, about 55 mg/day, about 60 mg/day, about 65 mg/day, about 70 mg/day, about 75 mg/day, about 80 mg/day, about 85 mg/day, about 90 mg/day, about 95 mg/day, about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day. Dosages may be administered more than one time per day (e.g., two, three, four, or more times per day). In one embodiment, a suitable dose of a PPARδ agonist, or a pharmaceutically acceptable salt thereof, for administration to a human is about 100 mg twice/day (i.e., a total of about 200 mg/day). In another embodiment, a suitable dose of a PPARδ agonist, or a pharmaceutically acceptable salt thereof, for administration to a human is about 50 mg twice/day (i.e., a total of about 100 mg/day).

In some aspects of the invention, PPARδ agonist is administered in a therapeutically effective amount to a subject (e.g., a human). As used herein, the term "effective amount" or "therapeutically effective amount" refers to an amount of an active ingredient that elicits the desired biological or medicinal response, for example, reduction or alleviation of the symptoms of the condition being treated. In some embodiments of the invention, the amount of PPARδ agonist administered can vary depending on various factors, including, but not limited to, the weight of the subject, the nature and/or extent of the subject's condition, etc.

Compounds

A peroxisome proliferator activated receptor-delta (PPARδ) agonist is a fatty acid, lipid, protein, peptide, small molecule, or other chemical entity that binds to the cellular PPARδ and elicits a downstream response, namely gene transcription, either native gene transcription or a reporter construct gene transcription, comparable to endogenous ligands such as retinoic acid or comparable to a standard reference PPARδ agonist such as carbacyclin.

In an embodiment, a PPARδ agonist is a selective agonist. As used herein, a selective PPARδ agonist is viewed as a chemical entity that binds to and activates the cellular PPARδ and does not substantially activate the cellular peroxisome proliferator activated receptors-alpha (PPARα) and -gamma (PPARγ). As used herein, a selective PPARδ agonist is a chemical entity that has at least a 10-fold maximum activation (as compared to endogenous receptor ligand) with a greater than 100-fold potency for activation of PPARδ relative to either or both of PPARα and PPARγ. In a further embodiment, a selective PPARδ agonist is a chemical entity that binds to and activates the cellular human PPARδ and does not substantially activate either or both of human PPARα and PPARγ. In a further embodiment, a selective PPARδ agonist is a chemical entity that has at least a 10 fold, or a 20 fold, or a 30 fold, or a 40 fold, or a 50 fold, or a 100 fold potency for activation of PPARδ relative to either or both of PPARα and PPARγ.

"Activation" here is defined as the abovementioned downstream response, which in the case of PPAR's is gene transcription. Gene transcription may be measured indirectly as downstream production of proteins reflective of the activation of the particular PPAR subtype under study. Alternatively, an artificial reporter construct may be employed to study the activation of the individual PPAR's expressed in cells. The ligand binding domain of the particular receptor to be studied may be fused to the DNA binding domain of a transcription factor, which produces convenient laboratory readouts, such as the yeast GAL4 transcription factor DNA binding domain. The fusion protein may be transfected into a laboratory cell line along with a Gal4 enhancer, which effects the expression of the luciferase protein. When such a system is transfected into a laboratory cell line, binding of a receptor agonist to the fusion protein will result in light emission.

A selective PPARδ agonist may exemplify the above gene transcription profile in cells selectively expressing PPARδ, and not in cells selectively expressing PPARγ or PPARα. In an embodiment, the cells may be expressing human PPARδ, PPARγ, and PPARα, respectively.

In a further embodiment, a PPARγ agonist may have an EC50 value of less than 5 m as determined by the PPAR transient transactivation assay described below. In an embodiment, the EC50 value is less than 1 m. In another embodiment, the EC50 value is less than 500 nM. In another embodiment, the EC50 value is less than 100 nM. In another embodiment, the EC50 value is less than 50 nM.

The PPAR transient transactivation assay may be based on transient transfection into human HEK293 cells of two plasmids encoding a chimeric test protein and a reporter protein respectively. The chimeric test protein may be a fusion of the DNA binding domain (DBD) from the yeast GAL4 transcription factor to the ligand binding domain (LBD) of the human PPAR proteins. The PPAR-LBD moiety harbored in addition to the ligand binding pocket also has the native activation domain, allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Cell Culture and Transfection:

HEK293 cells may be grown in DMEM+10% FCS. Cells may be seeded in 96-well plates the day before transfection to give a confluency of 50-80% at transfection. A total of 0.8 mg DNA containing 0.64 mg pM1a/gLBD, 0.1 mg pCM-VbGal, 0.08 mg pGL2(Gal4)$_5$, and 0.02 mg pADVANTAGE may be transfected per well using FuGene transfection reagent according to the manufacturer's instructions. Cells may be allowed to express protein for 48 h followed by addition of compound.

Plasmids:

Human PPARγ may be obtained by PCR amplification using cDNA synthesized by reverse transcription of mRNA from human liver, adipose tissue, and plancenta, respectively. Amplified cDNAs may be cloned into pCR2.1 and sequenced. The ligand binding domain (LBD) of each PPAR isoform may be generated by PCR (PPARδ: aa 128—C-terminus) and fused to the DNA binding domain (DBD) of the yeast transcription factor GAL4 by subcloning fragments in frame into the vector pM1 (Sadowski et al. (1992), Gene 118, 137), generating the plasmids pM1αLBD, pM1γLBD, and pM16. Ensuing fusions may be verified by sequencing.

The reporter may be constructed by inserting an oligonucleotide encoding five repeats of the GAL4 recognition sequence (Webster et al. (1988), Nucleic Acids Res. 16, 8192) into the vector pGL2 promotor (Promega), generating the plasmid pGL2(GAL4)$_5$. pCMVbGal may be purchased from Clontech and pADVANTAGE may be purchased from Promega.

Compounds:

Compounds may be dissolved in DMSO and diluted 1:1000 upon addition to the cells. Compounds may be tested in quadruple in concentrations ranging from 0.001 to 300 µM. Cells may be treated with compound for 24 h followed by luciferase assay. Each compound may be tested in at least two separate experiments.

Luciferase Assay:

Medium including test compound may be aspirated and 100 µl PBS including 1 mM $Mg^{++}$ and $Ca^{++}$ may be added to each well. The luciferase assay may be performed using the LucLite kit according to the manufacturer's instructions (Packard Instruments). Light emission may be quantified by counting on a Packard LumiCounter. To measure β-galactosidase activity, 25 ml supernatant from each transfection lysate may be transferred to a new microplate. β-Galactosidase assays may be performed in the microwell plates using a kit from Promega and read in a Labsystems Ascent Multiscan reader. The β-galactosidase data may be used to normalize (transfection efficiency, cell growth, etc.) the luciferase data.

Statistical Methods:

The activity of a compound may be calculated as fold induction compared to an untreated sample. For each compound, the efficacy (maximal activity) may be given as a relative activity compared to Wy14,643 for PPARα, rosiglitazone for PPARγ, and carbacyclin for PPARδ. The EC50 is the concentration giving 50% of maximal observed activity. EC50 values may be calculated via non-linear regression using GraphPad PRISM 3.02 (GraphPad Software, San Diego, Calif.).

In a further embodiment, a PPARδ agonist has a molecular weight of less than 1000 g/mol, or a molecular weight of less than 950 g/mol, or a molecular weight of less than 900 g/mol, or a molecular weight of less than 850 g/mol, or a molecular weight of less than 800 g/mol, or a molecular weight of less than 750 g/mol, or a molecular weight of less than 700 g/mol, or a molecular weight of less than 650 g/mol, or a molecular weight of less than 600 g/mol, or a molecular weight of less than 550 g/mol, or a molecular weight of less than 500 g/mol, or a molecular weight of less than 450 g/mol, or a molecular weight of less than 400 g/mol, or a molecular weight of less than 350 g/mol, or a molecular weight of less than 300 g/mol, or a molecular weight of less than 250 g/mol. In another embodiment, a PPARδ agonist has a molecular weight of greater than 200 g/mol, or a molecular weight of greater than 250 g/mol, or a molecular weight of greater than 250 g/mol, or a molecular weight of greater than 300 g/mol, or a molecular weight of greater than 350 g/mol, or a molecular weight of greater than 400 g/mol, or a molecular weight of greater than 450 g/mol, or a molecular weight of greater than 500 g/mol, or a molecular weight of greater than 550 g/mol, or a molecular weight of greater than 600 g/mol, or a molecular weight of greater than 650 g/mol, or a molecular weight of greater than 700 g/mol, or a molecular weight of greater than 750 g/mol, or a molecular weight of greater than 800 g/mol, or a molecular weight of greater than 850 g/mol, or a molecular weight of greater than 900 g/mol, or a molecular weight of greater than 950 g/mol, or a molecular weight of greater than 1000 g/mol. Any of the upper and lower limits described above in this paragraph may be combined.

In an embodiment, a PPARδ agonist may be a PPARδ agonist compound as disclosed in any of the following published patent applications: WO 97/027847, WO 97/027857, WO 97/028115, WO 97/028137, WO 97/028149, WO 98/027974, WO 99/004815, WO 2001/000603, WO 2001/025181, WO 2001/025226, WO 2001/034200, WO 2001/060807, WO 2001/079197, WO 2002/014291, WO 2002/028434, WO 2002/046154, WO 2002/050048, WO 2002/059098, WO 2002/062774, WO 2002/070011, WO 2002/076957, WO 2003/016291, WO 2003/024395, WO 2003/033493, WO 2003/035603, WO 2003/072100, WO 2003/074050, WO 2003/074051, WO 2003/074052, WO 2003/074495, WO 2003/084916, WO 2003/097607, WO 2004/000315, WO 2004/000762, WO 2004/005253, WO 2004/037776, WO 2004/060871, WO 2004/063165, WO 2004/063166, WO 2004/073606, WO 2004/080943, WO 2004/080947, WO 2004/092117, WO 2004/092130, WO 2004/093879, WO 2005/060958, WO 2005/097098, WO 2005/097762, WO 2005/097763, WO 2005/115383, WO 2006/055187, WO 2007/003581, and WO 2007/071766.

In another embodiment, a PPARδ agonist may be a compound selected from the group consisting of sodelglitazar; lobeglitazone; netoglitazone; and isaglitazone;

2-[2-methyl-4-[[3-methyl-4-[[4-(trifluoromethyl)phenyl]methoxy]phenyl]thio]phenoxy]-acetic acid (See WO 2003/024395);

(S)-4-[cis-2,6-dimethyl-4-(4-trifluoromethoxy-phenyl)piperazine-1-sulfonyl]-indan-2-carboxylic acid or a tosylate salt thereof (KD-3010);

4-butoxy-a-ethyl-3-[[[2-fluoro-4-(trifluoromethyl)benzoyl]amino]methyl]-benzenepropanoic acid (TIPP-204);

2-[2-methyl-4-[[[4-methyl-2-[4-(trifluoromethyl)phenyl]-5-thiazolyl]methyl]thio]phenoxy]-acetic acid (GW-501516);

2-[2,6 dimethyl-4-[3-[4-(methylthio)phenyl]-3-oxo-1(E)-propenyl]phenoxyl]-2-methylpropanoic acid (GFT-505); and {2-methyl-4-[5-methyl-2-(4-trifluoromethyl-phenyl)-2H-[1,2,3]triazol-4-ylmethylsylfanyl]-phenoxy}-acetic acid.

In an embodiment, a PPARδ agonist is (Z)-[2-Methyl-4-[3-(4-methylphenyl)-3-[4-[3-(morpholin-4-yl)propynyl]phenyl]allyloxy]-phenoxy]acetic acid:

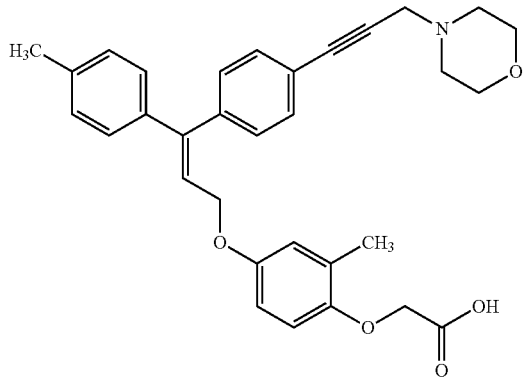 [SMILES: Cc1ccc(/C(=C/COc2ccc(OCC(=O)O)c(C)c2)c2ccc(C#CCN3CCOCC3)cc2)cc1]

An example of the chemical synthesis of (Z)-[2-Methyl-4-[3-(4-methylphenyl)-3-[4-[3-(morpholin-4-yl)propynyl]phenyl]allyloxy]-phenoxy]acetic acid may be found in Example 3 of PCT Application Pub. No. WO 2007/071766.

In an embodiment, a PPARδ agonist is (E)-[2-Methyl-4-[3-[4-[3-(pyrazol-1-yl)prop-1-ynyl]phenyl]-3-(4-trifluoromethylphenyl)-allyloxy]phenoxy]acetic acid:

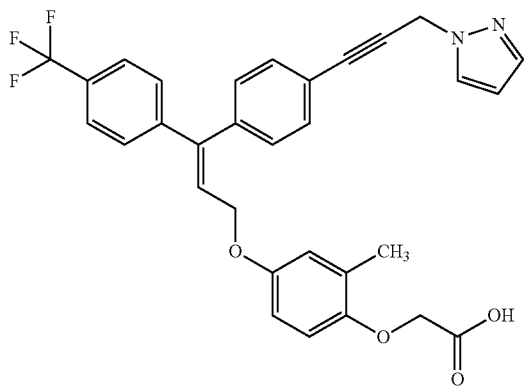 [SMILES: Cc1cc(OC/C=C(\c2ccc(C#CCn3cccn3)cc2)c2ccc(C(F)(F)F)cc2)ccc1OCC(=O)O]

An example of the chemical synthesis of (E)-[2-Methyl-4-[3-[4-[3-(pyrazol-1-yl)prop-1-ynyl]phenyl]-3-(4-trifluoromethylphenyl)-allyloxy]phenoxy]acetic acid may be found in Example 4 of PCT Application Pub. No. WO 2007/071766.

In an embodiment, a PPARδ agonist is (E)-[4-[3-(4-Fluorophenyl)-3-[4-[3-(morpholin-4-yl)propynyl]phenyl]allyloxy]-2-methyl-phenoxy]acetic acid:

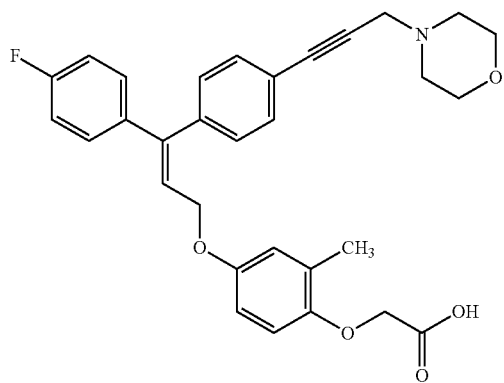 [SMILES: Cc1cc(OC/C=C(/c2ccc(F)cc2)c2ccc(C#CCN3CCOCC3)cc2)ccc1OCC(=O)O]

An example of the chemical synthesis of (E)-[4-[3-(4-Fluorophenyl)-3-[4-[3-(morpholin-4-yl)propynyl]phenyl]allyloxy]-2-methyl-phenoxy]acetic acid may be found in Example 10 of PCT Application Pub. No. WO 2007/071766.

In an embodiment, a PPARδ agonist is (E)-[2-Methyl-4-[3-[4-[3-(morpholin-4-yl)propynyl]phenyl]-3-(4-trifluoromethylphenyl)allyloxy]-phenoxy]acetic acid:

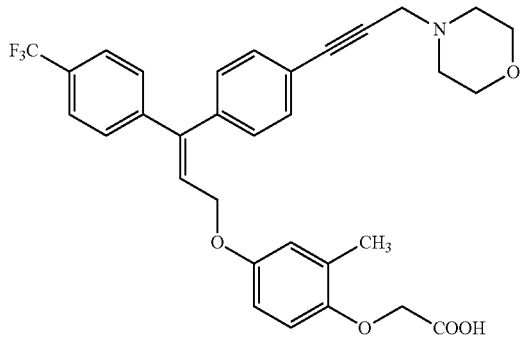 [SMILES: Cc1cc(OC/C=C(\c2ccc(C#CCN3CCOCC3)cc2)c2ccc(C(F)(F)F)cc2)ccc1OCC(=O)O]

An example of the chemical synthesis of (E)-[2-Methyl-4-[3-[4-[3-(morpholin-4-yl)propynyl]phenyl]-3-(4-trifluoromethylphenyl)allyloxy]-phenoxy]acetic acid may be found in Example 20 of PCT Application Pub. No. WO 2007/071766.

In an embodiment, a PPARδ agonist is (E)-[4-[3-(4-Chlorophenyl)-3-[4-[3-(morpholin-4-yl)propynyl]phenyl]allyloxy]-2-methyl-phenoxy]acetic acid:

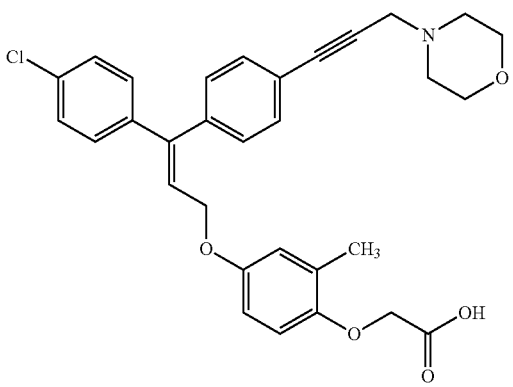 [SMILES: Cc1cc(OC/C=C(/c2ccc(Cl)cc2)c2ccc(C#CCN3CCOCC3)cc2)ccc1OCC(=O)O]

An example of the chemical synthesis of (E)-[4-[3-(4-Chlorophenyl)-3-[4-[3-(morpholin-4-yl)propynyl]phenyl]allyloxy]-2-methyl-phenoxy]acetic acid may be found in Example 46 of PCT Application Pub. No. WO 2007/071766.

In an embodiment, a PPARδ agonist is (E)-[4-[3-(4-Chlorophenyl)-3-[4-[3-(morpholin-4-yl)propynyl]phenyl]allyloxy]-2-methylphenyl]-propionic acid:

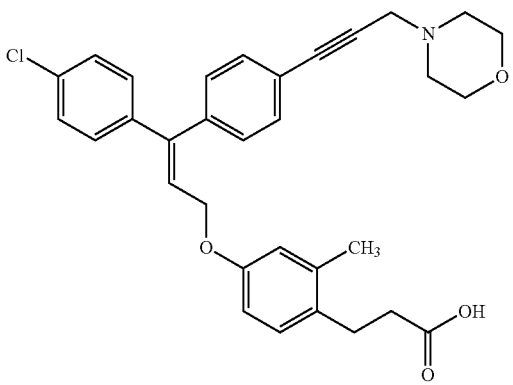 [SMILES: Cc1cc(OC/C=C(/c2ccc(Cl)cc2)c2ccc(C#CCN3CCOCC3)cc2)ccc1CCC(=O)O]

An example of the chemical synthesis of (E)-[4-[3-(4-Chlorophenyl)-3-[4-[3-(morpholin-4-yl)propynyl]phenyl]allyloxy]-2-methylphenyl]-propionic acid may be found in Example 63 of PCT Application Pub. No. WO 2007/071766.

In an embodiment, a PPARδ agonist is {4-[3-Isobutoxy-5-(3-morpholin-4-yl-prop-1-ynyl)-benzyl sulfanyl]-2-methyl-phenoxy}-acetic acid:

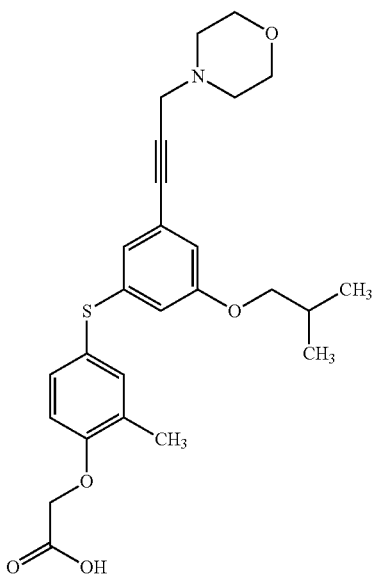 [SMILES: Cc1cc(Sc2cc(C#CCN3CCOCC3)cc(OCC(C)C)c2)ccc1OCC(=O)O]

An example of the chemical synthesis of {4-[3-Isobutoxy-5-(3-morpholin-4-yl-prop-1-ynyl)-benzylsulfanyl]-2-methyl-phenoxy}-acetic acid may be found in Example 9 of PCT Application Pub. No. WO 2007/003581.

In an embodiment, a PPARδ agonist is {4-[3-Isobutoxy-5-(3-morpholin-4-yl-prop-1-ynyl)-phenylsulfanyl]-2-methyl-phenoxy}-acetic acid:

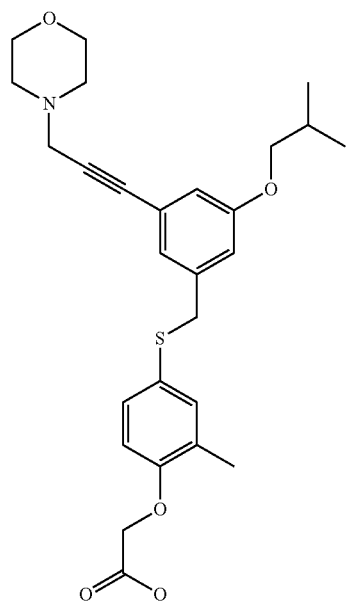 [SMILES: Cc1cc(SCc2cc(C#CCN3CCOCC3)cc(OCC(C)C)c2)ccc1OCC(=O)O]

An example of the chemical synthesis of {4-[3-Isobutoxy-5-(3-morpholin-4-yl-prop-1-ynyl)-phenylsulfanyl]-2-methyl-phenoxy}-acetic acid may be found in Example 35 of PCT Application Pub. No. WO 2007/003581.

In an embodiment, a PPARδ agonist is {4-[3,3-Bis-(4-bromo-phenyl)-allyloxy]-2-methyl-phenoxy}-acetic acid:

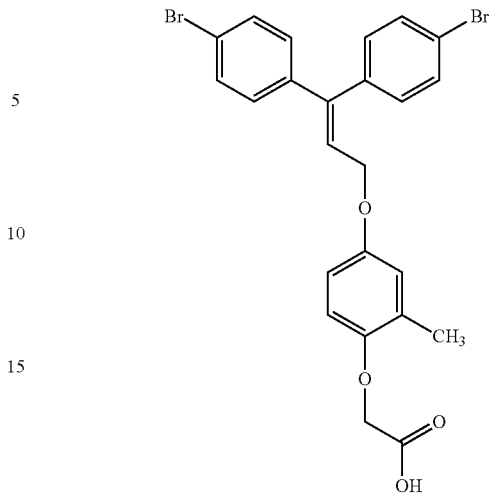

An example of the chemical synthesis of {4-[3,3-Bis-(4-bromo-phenyl)-allyloxy]-2-methyl-phenoxy}-acetic acid may be found in Example 10 of PCT Application Pub. No. WO 2004/037776.

Accordingly, in an embodiment, a PPARδ agonist may be a compound selected from the group consisting of:

(Z)-[2-Methyl-4-[3-(4-methylphenyl)-3-[4-[3-(morpholin-4-yl)propynyl]phenyl]allyloxy]-phenoxy]acetic acid;

(E)-[2-Methyl-4-[3-[4-[3-(pyrazol-1-yl)prop-1-ynyl]phenyl]-3-(4-trifluoromethylphenyl)-allyloxy]phenoxy]acetic acid;

(E)-[4-[3-(4-Fluorophenyl)-3-[4-[3-(morpholin-4-yl)propynyl]phenyl]allyloxy]-2-methyl-phenoxy]acetic acid;

(E)-[2-Methyl-4-[3-[4-[3-(morpholin-4-yl)propynyl]phenyl]-3-(4-trifluoromethylphenyl)allyloxy]-phenoxy]acetic acid;

(E)-[4-[3-(4-Chlorophenyl)-3-[4-[3-(morpholin-4-yl)propynyl]phenyl]allyloxy]-2-methyl-phenoxy]acetic acid;

(E)-[4-[3-(4-Chlorophenyl)-3-[4-[3-(morpholin-4-yl)propynyl]phenyl]allyloxy]-2-methylphenyl]-propionic acid;

{4-[3-Isobutoxy-5-(3-morpholin-4-yl-prop-1-ynyl)-benzylsulfanyl]-2-methyl-phenoxy}-acetic acid;

{4-[3-Isobutoxy-5-(3-morpholin-4-yl-prop-1-ynyl)-phenylsulfanyl]-2-methyl-phenoxy}-acetic acid; and {4-[3,3-Bis-(4-bromo-phenyl)-allyloxy]-2-methyl-phenoxy}-acetic acid; or a pharmaceutically acceptable salt thereof.

In a further embodiment, a PPARδ agonist is (E)-[4-[3-(4-Fluorophenyl)-3-[4-[3-(morpholin-4-yl)propynyl]phenyl]allyloxy]-2-methyl-phenoxy]acetic acid or a pharmaceutically acceptable salt thereof.

As used throughout this specification, the term "pharmaceutically acceptable salt" refers to salts of a free acid or a free base that are not biologically undesirable and are generally prepared by reacting the free base with a suitable organic or inorganic acid or by reacting the acid with a suitable organic or inorganic base. The term may be used in reference to any compound of the present invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium, and Valerate. When an acidic substituent is present, such as —COOH, there can be formed the ammonium, morpholinium, sodium, potassium, barium, calcium salt, and the like for use as the dosage form. When a basic group is present, such as amino, or a basic heteroaryl radical, such as pyridyl, there can be formed an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate, and the like, and include acids related to the pharmaceutically acceptable salts listed in Stephen M. Berge, et al., Journal of Pharmaceutical Sciences, Vol. 66(1), pp. 1-19 (1977).

Pharmaceutical Compositions

In some embodiments of the invention, a PPARδ agonist may be included within a pharmaceutical composition. As used herein, the term "pharmaceutical composition" refers to a liquid or solid composition, preferably solid (e.g., a granulated powder), that contains a pharmaceutically active ingredient (e.g., a PPARδ agonist) and at least a carrier, where none of the ingredients is generally biologically undesirable at the administered quantities.

Pharmaceutical compositions incorporating a PPARδ agonist may take any physical form that is pharmaceutically acceptable. Pharmaceutical compositions for oral administration are particularly preferred. In one embodiment of such pharmaceutical compositions, an effective amount of a PPARδ agonist is incorporated.

The inert ingredients and manner of formulation of the pharmaceutical compositions of the invention are conventional. Known methods of formulation used in pharmaceutical science may be followed. All of the usual types of compositions are contemplated, including, but not limited to, tablets, chewable tablets, capsules, and solutions. The amount of the PPARδ agonist, however, is best defined as the effective amount, that is, the amount of the PPARδ agonist that provides the desired dose to the subject in need of such treatment. The activity of the PPARδ agonists does not depend on the nature of the composition, so the compositions may be chosen and formulated solely for convenience and economy. Any of the PPARδ agonists as described herein may be formulated in any desired form of composition.

Capsules may be prepared by mixing the PPARδ agonist with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets may be prepared by direct compression, by wet granulation, or by dry granulation. Their formulations usually incorporate diluents, binders, lubricants, and disintegrators, as well as the PPARδ agonist. Typical diluents include, for example, various types of starch, lactose, mannitol, kaolin, calcium phosphate or sulfate, inorganic salts such as sodium chloride, and powdered sugar. Powdered cellulose derivatives are also useful. Typical tablet binders are substances such as starch, gelatin, and sugars such as lactose, fructose, glucose, and the like. Natural and synthetic gums are also convenient, including acacia, alginates, methylcellulose, polyvinylpyrrolidine, and the like. Polyethylene glycol, ethylcellulose, and waxes can also serve as binders.

A lubricant in a tablet formulation may help prevent the tablet and punches from sticking in the die. A lubricant can be chosen from such solids as talc, magnesium and calcium stearate, stearic acid, and hydrogenated vegetable oils.

Tablet disintegrators are substances that swell when wetted to break up the tablet and release the compound. They include starches, clays, celluloses, aligns, and gums. More particularly, corn and potato starches, methylcellulose, agar, bentonite, wood cellulose, powdered natural sponge, cation-exchange resins, alginic acid, guar gum, citrus pulp, and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate, and hydroxypropyl methylcellulose acetate succinate.

Tablets are often coated with sugar as a flavor and sealant. The PPARδ agonists may also be formulated as chewable tablets by using large amounts of pleasant-tasting substances such as mannitol in the formulation, as is now well-established practice.

Transdermal patches may be used. Typically, a patch comprises a resinous composition in which the active compound(s) will dissolve, or partially dissolve, and is held in contact with the skin by a film that protects the composition. Other, more complicated patch compositions are also in use, particularly those having a membrane pierced with innumerable pores through which the drugs are pumped by osmotic action.

In any embodiment where a PPARδ agonist is included in a pharmaceutical composition, such pharmaceutical compositions may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate, or sodium phosphate; granulating and disintegrating agents, for example, corn starch or alginic acid; binding agents, for example, starch, gelatin, or acacia; and lubricating agents, for example, magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Protocol

A protocol for the experimental evaluation of the impact of a PPARδ agonist on muscle atrophy during and following the end of limb immobilization is provided below. In the protocol, reference to Compound 1 refers to (E)-[4-[3-(4-Fluorophenyl)-3-[4-[3-(morpholin-4-yl)propynyl]phenyl]allyloxy]-2-methyl-phenoxy]acetic acid sodium salt.

A randomized, investigator and subject blind, sponsor open, placebo-controlled study evaluating the possible impact of Compound 1 on the recovery of muscle atrophy from limb immobilization is described. Subjects will be leg immobilized using a knee brace (30 degrees flexion on the left leg to allow driving) and will be provided with walking crutches such that there is no weight bearing on the immobilized leg. Subjects will be enrolled and randomized to receive Compound 1 or placebo (both referenced as Study Drug in this protocol). The study consists of five periods termed SCR (screening period, Day −35 to −3), BL (baseline period: Day −1 to Day 1 [am]), IMM (limb immobilization and treatment with study drug, Day 1 [pm] to Day 14), TRE (treatment with study drug without limb immobilization, Day 15 to Day 29) and REC (no treatment recovery period, Day 29 to Day 42). There will be six testing days during the study: Day 1 (baseline), Day 14 (brace off day), Day 16 (48 hours after brace off), Day 21, Day 29 (last dose) and Day 42 (final study visit). On each testing day, subjects will undergo the combination of several testing procedures in sequential order as listed: 1) Morning activity plus approximately 500-step walk (when domiciled at Clinical Research Unit [CRU]); 2) Blood sampling; 3) Standardized breakfast (Study Drug administration will be immediately before the breakfast except for Day 42); 4) Muscle biopsy; 5) Leg muscle strength tests (MST) and modified physical performance test (PPT); and 6) Magnetic resonance imaging (MRI) of the thigh to evaluate thigh muscle volume/cross-section area (CSA).

Baseline testing (Day 1 [am]) and testing on day 14 and 16 will be performed after subjects have been admitted to the Clinical Research Unit (CRU). On Day −1 (before baseline testing), subjects will be admitted to the CRU in the evening after having been instructed to abstain from exercise, to ingest a standard weight-maintaining diet, and to avoid caffeine and alcohol for three days before being admitted to the CRU. At 1900 h on Day −1, they will consume a standardized meal and then fast (except for water) and rest in bed until the next morning. At 0730 h on Day 1, they will be asked to use the bathroom, shower, brush their teeth, and walk (approximately 500 steps). At 0800 h, subjects will undergo the testing procedures (including breakfast) described above. After completion of all testing procedures, subjects will receive lunch and will then be fitted with the knee brace. Subjects will stay at the CRU until evening Study Drug dosing time. The first dose of the study drug will be administered by the site staff on site around 1900 h and dinner will be provided immediately after dosing. Subjects will be discharged from the CRU with study drug supply and instructions for at home self-administration. Subjects will be encouraged to walk between 4,000 and 6,000 steps per day for the duration of the study (Day 1-Day 42) unless otherwise specified.

An outpatient visit at Day 6 (±1 day) will be scheduled for safety labs and PK trough level. Subject should be fasted overnight before the visit and the Study Drug will be administered at the study site immediately before breakfast is served.

On Day 13 (−1 day window), (one day before the end of limb immobilization), subjects will be admitted to the CRU in the evening after having been instructed to ingest a standard weight-maintaining diet and to avoid caffeine and alcohol for three days before being admitted to the CRU. At 1900 h, they will consume a standardized meal and then fast (except for water) and rest in bed until the next morning (Day 14). At 0700 h on Day 14, the knee brace will be removed and subjects will be asked to use the bathroom, shower, brush their teeth, and walk (approximately 500 steps). At 0800 h, subjects will take the study drug under the supervision of site staff and undergo the testing procedures (including breakfast) described above. After completion of all testing procedures subjects will return to the CRU, where they will receive lunch, a snack later in the afternoon, and a standardized dinner as described above at 1900 h. They will also be encouraged to take short walks to total 2000 steps (±250 steps) on day 14. On day 15, they will receive standardized meals the same as in Day 14 and will rest in a chair in the CRU except for 4 brief periods of walking approximately 500 steps each (2000 steps total±250 steps for entire day). On day 16 (testing day), subjects will be asked to use the bathroom, shower, brush their teeth, and walk (approximately 500 steps) at 0730 h. At 0800 h, they will undergo the testing procedures (including breakfast) described above. After completion of all testing procedures, subjects will receive lunch and will be discharged from the CRU.

On days 21, 29, and 42 (±1 day), subjects will be tested as outpatients in the CRU after having been instructed to consume a weight maintaining diet and no caffeine for at least 3 days before the study visit. They will arrive in the CRU before 0800 h after an overnight fast, blood sample should be collected around 0800 h, and the study drug should be administered right after. The standardized breakfast will be provided immediately after dosing (except for Day 42) and then testing undergone as described previously.

Two treatment groups in this study:
 a) Treatment group A: Treated with 100 mg of Compound 1 twice daily from Day 1 to Day 29.
 b) Treatment group B: Treated with placebo twice daily from Day 1 to Day 29.

If there is a weight gain at the end of the study (Day 42), a weight loss program will be provided as an option to all subjects.

Diagnosis and Main Criteria for Inclusion:
Key inclusion criteria: 1) Healthy males aged 30 to 55 years, inclusive, at the time of screening; 2) Subjects must be in good health, as determined by medical history, physical examination, vital signs, electrocardiogram (ECG), and clinical test results; 3) Not restricted to a wheel-chair or confined to a bed; 4) Weight ≥50.0 kg; and 5) BMI between 18 and 30.0 kg/m$^2$, inclusive, at the time of screening. Key exclusion criteria: 1) Fasting glucose >110 mg/dL (Screening Visit only); 2) Serum creatinine >1.5 mg/dL (Screening Visit and Baseline; if serum creatinine is >1.5 mg/dL and creatinine clearance is >60 mL/min, the subject need not be excluded); 3) Troponin I level above the upper limit of normal (ULN; Screening Visit and Baseline); 4) Liver function tests (LFTs) >1.5×ULN (Screening Visit and Baseline); 5) Evidence of significant organ system dysfunction (e.g., diabetes, cardiovascular disease, cirrhosis, hypogonadism, hypo- or hyperthyroidism; hypertension); 6) Any fluctuations in weight (no more than +2% of body weight) by subject self-report in the 3 months prior to the Screening Visit; 7) Had received Compound 1 in a previous clinical trial; 8) Smoking within 6 month prior to Day −1; and 9) Michigan Alcohol Screening Test score greater than 2.

Safety Criteria:
Adverse events (AEs), clinical laboratory tests, vital signs, 12-lead electrocardiogram (ECG), and physical examinations.

All safety analyses will be based on the safety population, comprising all subjects who are randomized to a treatment group and subsequently receive study medication. Safety variables will be summarized using descriptive statistics (mean, standard deviation, median, range, and number of observations).

Pharmacokinetics (PK):

Trough PK of Compound 1 at 100 mg BID (twice daily) during 28 days of treatment. Blood samples for assessment of Compound 1 plasma trough concentrations will be collected throughout the study. Pre-dose (t=0) blood draws for PK samples were taken within 10 minutes prior to dosing on Day 6, 14, 16, 21, and 29. Plasma samples collected from subjects receiving Compound 1 were analyzed for Compound 1 concentrations using a previously developed and validated bioanalytical method.

All PK analyses will be based on the PK population, comprising all subjects who received Compound 1. All derived PK parameters, and plasma Compound 1 concentrations at each scheduled assessment time point, will be summarized with descriptive statistics (arithmetic and geometric mean, standard deviation, coefficient of variation, median, range, and number of observations). Graphical displays of individual subject and mean plasma Compound 1 concentrations across time will also be generated.

Pharmacodynamics (PD):

PD parameters will be assessed at baseline (Day 1 [am]), Day 14, Day 16, Day 21, Day 29, and Day 42 to measure the changes from baseline to Day 14, from Day 14 to Day 16, from Day 14 to Day 21, from Day 14 to Day 29, and from Day 14 to Day 42. PD parameters will be: 1) Muscle Strength Test (MST); 2) Physical Performance Test (PPT); 3) muscle cross section area (CSA) measurement (via Magnetic Resonance Imaging [MRI]); and 4) muscle tissue biomarker measurement (muscle biopsy). Biomarkers evaluated from muscle tissue were: 1) Gene Expression Analysis (Global Gene Array); 2) PCG-1α downstream gene profile; 3) Micro RNA; 4) Protein Content (phospho-mTOR, mTOR, Ub, CS, COX subunit II, COX subunit IV); 5) Enzyme Analysis (Citrate Synthase, COX); and 6) Muscle fiber size. A CSA MRI will not be performed on Day 16, and biomarkers from muscle tissue will not be evaluated on Day 42.

PD sample collection time will be subject to the available schedule of each procedure on each of the test days. Blood samples will be collected within 1 hour of dosing (t=0). Breakfast will be provided at 0800 h (±1 hour) immediately after dosing. Muscle biopsy (not performed on Day 42) will be performed at 1000 h (2 hours±15 minutes reference to breakfast time). Muscle strength and physical performance testing will be performed after muscle biopsy. Magnetic resonance imaging (MRI) of the thigh will be performed last (not performed on Day 16).

After an overnight fast, approximately 30 ml of venous (antecubital) blood will be collected within 1 hour of dosing time (0800 h), to measure safety labs and the following PD parameters: glucose, insulin, hsCRP, Lipid panel (HDL-c, LDL-c, Total Cholesterol, and Triglycerides). Blood samples for the determination of glucose concentration will be collected in chilled tubes containing heparin and analyzed immediately after collection.

A punch biopsy from the quadriceps femoris (~100 mg) will be obtained through a small cutaneous incision during local anesthesia (lidocain, 2%). An aliquot of the muscle tissue will be embedded in TissueTek® for histology; the remaining muscle tissue will be immediately rinsed in ice-cold homogenization buffer (50 mM Tris-HCl pH 7.5, 1 mM EDTA, 1 mM EGTA, 10 mM glycerophosphate, 50 mM NaF, 0.1% Triton-X, 0.1% 2-mercaptoethanol, 1 complete protease/phosphatase inhibitor tablet [Roche Diagnostics Ltd, Burgess Hill, UK]) or buffered saline, cleaned off connective tissue and blood, split into two aliquots (one aliquot should be around 40 mg) and submerged in liquid nitrogen and then stored at −80° C. until further processing.

The Muscle Strength Test (MST):

The maximal amount of weight that the participant is able to lift for one repetition (1-RM) will be measured on a Hoist multi-station weight machine for the following exercises: leg press, knee extension, knee flexion, and bench press. Isokinetic (Cybex) testing of knee extension/flexion will be done to assess deficiencies in rapid strength recruitment. Subjects will be seated on the testing device and strapped in to prevent the pelvis from sliding forward. The movement arm will be adjusted to the subject's leg length and the weight of the leg will be determined. Isokinetic testing of the knee extensors and flexors will be performed at 0°/s, 60°/s and 180°/s. Four to five repetitions at each mode will be performed with the highest two values used for data analysis. Subjects will be familiarized with these procedures during the screening visit.

The Physical Performance Test (PPT):

To objectively evaluate physical performance, we will administer the modified physical performance test (PPT). The modified PPT is a performance-based global measure of physical performance that evaluates the ability to perform usual daily activities, including both basic activities of daily living and instrumental activities of daily living. It includes 6 tasks that are timed: 1) climb a flight of 10 stairs, 2) stand up 5 times from a 16" high chair, 3) walk 50 ft, 4) put on and remove a coat, 5) pick up a penny placed 12" in front of the foot on the dominant side, and 6) lift a 7 lb book to a shelf ~12 in above shoulder height. The other 3 tasks include an evaluation of 1) the ability to climb up and down 4 flights of 10 stairs, 2) the performance of a 360° turn, and 3) standing balance with feet side-by-side, semi-tandem, and full-tandem.

Magnetic Resonance Imaging:

MRI will be used to quantify thigh muscle volume. Images will be acquired on a 1.5-T superconducting Siemens MRI scanner (Siemens, Iselin, N.J.) in the Human Imaging Unit facilities at Washington University School of Medicine. Bilateral T1-weighted axial images with and without fat saturation will be acquired using commercially available Siemens sequences starting 10 cm proximal to the distal edge of the femur and covering an approximate extent of 10 cm. After correcting/subtracting intramuscular fat, muscle volumes in each of the images will be determined by segmenting the cross-sectional muscle areas for each slice using Matlab software (Mathworks, Natick, Mass.) and summing the area by slice thickness for all slices. The analysis method will include a series of semi-automated steps such as image filtering/homogeneity correction, tissue identification by threshold analysis, manual review/correction of resulting classifications, and reporting of muscle volumes.

PD analysis will be based on the evaluable population. PD variables will be summarized with descriptive statistics (mean, standard deviation, median, range, and number of observations). Appropriate inferential analyses may be performed to evaluate treatment trends on change from baseline or between-group differences. In particular, there will be a matched pair analysis of each subject in the study. The analysis will compare PD variable levels prior to drug exposure with tests of subject plasma during each day of dosing and final study visit. Within-group change from baseline to Day 14, Day 14 to 16, Day 14 to 21, Day 14 to 29, and Day 14 to 42 and the differences among groups from baseline to Day 14, Day 14 to 16, Day 14 to 21, Day 14 to 29, and Day 14 to 42 will be assessed. Variables with skewed distributions will be log-transformed before analysis. If the data are not normally distributed after logarithmic transformation, appropriate nonparametric tests will be used.

The following example and associated results are provided as illustrations of some embodiments of the invention and are not intended to limit the scope of the claimed subject matter in any way.

EXAMPLES

In the Example below, reference to Compound 1 refers to (E)-[4-[3-(4-Fluorophenyl)-3-[4-[3-(morpholin-4-yl)propynyl]phenyl]allyloxy]-2-methyl-phenoxy]acetic acid sodium salt.

Example 1

An experimental study was conducted to evaluate the impact of Compound 1, a PPARδ agonist, on muscle atrophy during and following the end of limb immobilization in human subjects. Except where specifically noted otherwise below, all methods were conducted as described in the protocol above.

Methods

Methods were generally conducted as described in the protocol. The study was designed as a double-blind, randomized, placebo-controlled, parallel study in healthy male subjects. A total of N=24 subjects were randomized. The number of randomized subjects is lower than originally planned. A total of N=21 subjects had data available for statistical analysis. Despite statistical power below that typically used, statistically significant superiority over placebo was observed for the primary muscle strength variable of analysis.

The study randomized 24 subjects, 12 of whom were randomized to receive Compound 1 (mean age=42; 50% Black or African American) and 12 of whom were randomized to receive placebo (mean age=39; 58% Black or African American). One subject had no data post-baseline, and therefore did not provide usable data. Two other subjects also did not provide usable data.

Statistical analysis compared the experimental group treated with Compound 1 (n=10) with the placebo group (n=1). Dropout rates in the study were 17% in each treatment group.

During an unblinded interim analysis, it was revealed that three of the placebo-treated subjects increased in muscle strength and also in muscle volume during the immobilization period. Subsequently, a blinded data review included identification of any subject (regardless of treatment group) who had a significant increase during immobilization in muscle volume as measured by MRI, where a significant increase was defined as an increase of more than 1 standard deviation. A total of 4 subjects met this criterion, one of which was treated with Compound 1. The analysis conclusions, therefore, are considered to be conservative.

Multiple imputation statistical methods were used to preserve the intent-to-treat (ITT) principle while coping with invalid and missing data.

Primary analysis was executed as defined in the study protocol and the statistical analysis plan (see protocol described above). Supportive analysis included coping with missing data in different ways to ensure robustness of analysis conclusions against the methodology used. Methods included: (1) primary (multiple imputation based on recursive regression), (2) observed cases (no data suppression, no data imputation), (3) completers (stable group for longitudinal analysis, (4) ITT, last-observation-carried-forward (stable group, all patients), (5) per-protocol set per ICH E9 (excludes protocol violators), (6) use of placebo median imputed for missing data, and (7) use of placebo mean imputed for missing data. Analysis results indicated firm robustness against methodology.

Statistical analysis used analysis of covariance (ANCOVA) with baseline measure used as a covariate. The least-squares mean (LSMEAN) change is a mean change from baseline estimated from the ANCOVA model that reflects adjustment for baseline values.

Results

FIG. 1 shows a graph of mean changes from baseline in muscle strength representing the primary analysis (reflecting multiple imputation for missing and invalid data) of the effect of administration of Compound 1 on performance of a repeated measures knee extension strength test during (day 0 to day 14) and after (following day 14) limb immobilization in human subjects.

The data supporting the graph shown in FIG. 1 is also provided in Table 1 below.

TABLE 1

| Time | Statistic | Compound 1 (n = 10) | Placebo (n = 11) | Mean Difference | P-value (2-sample t-test) |
|---|---|---|---|---|---|
| Baseline | Mean | 195 | 176 | 19 | 0.3 |
| Day 14 | LSMean change | −2.9 | −38.9 | 36 | 0.012 |
| Day 21 (primary) | LSMean change | 36.8 | −0.3 | 36.5 | 0.004 |
| Day 29 | LSMean change | 30.4 | 8.5 | 21.9 | 0.2 |

Figure 2:
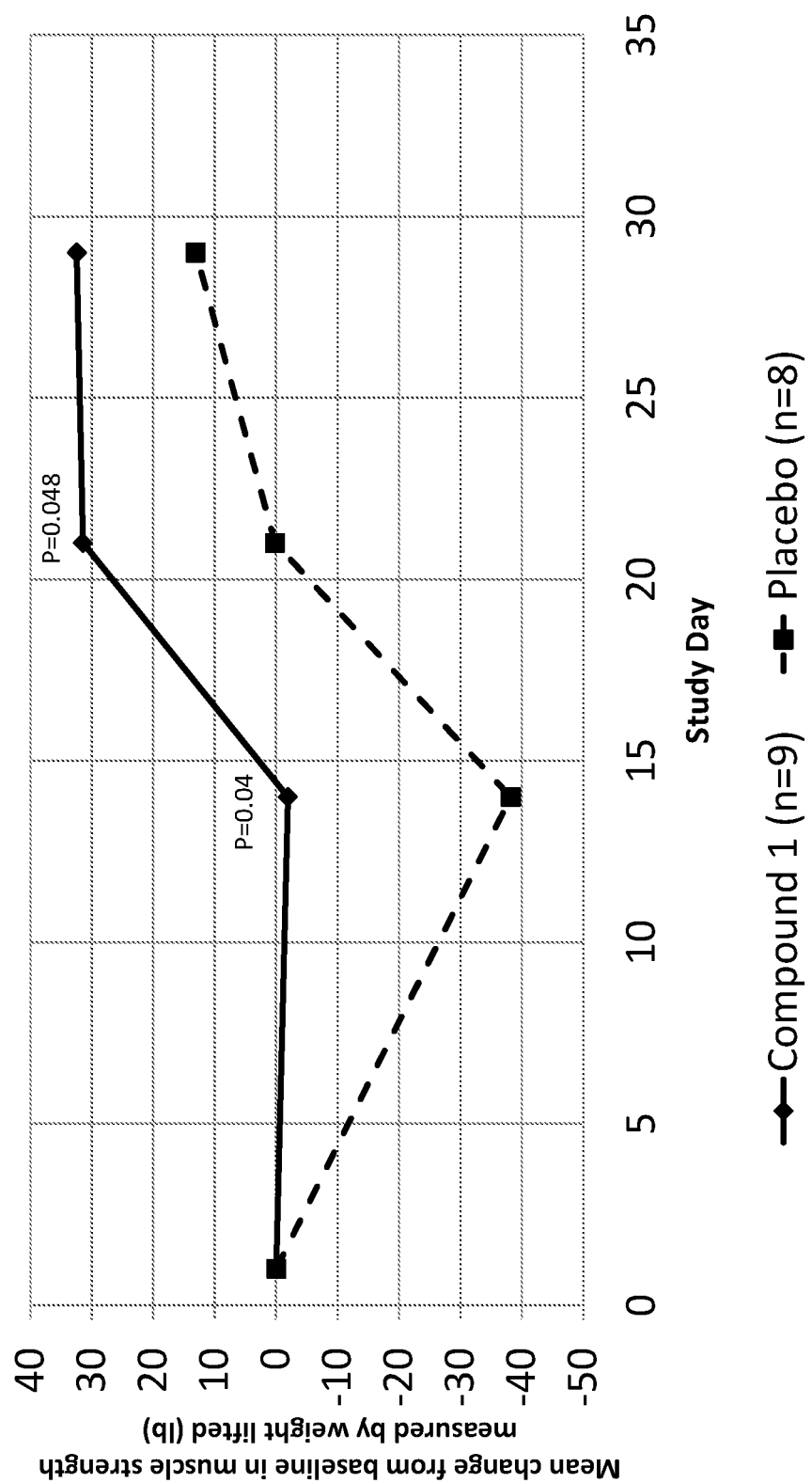
FIG. 2 shows a graph of mean changes from baseline in muscle strength representing the effect of administration of a PPARδ agonist on performance of a repeated measures knee extension strength test during (day 0 to day 14) and after (day 14 to day 21 and day 21 to day 29) limb immobilization in human subjects. Data reflects all available data for subjects with valid data, excluding protocol violators (i.e., no imputation for missing and invalid data).

FIG. 2 shows a graph of mean changes from baseline in muscle strength representing supportive analysis (using all available data for subjects with valid data, excluding protocol violators, i.e., no imputation) of the effect of administration of Compound 1 on performance of a repeated measures knee extension strength test during (day 0 to day 14) and after (day 14 to day 21 and day 21 to day 29) limb immobilization in human subjects.

The data supporting the graph shown in FIG. 2 is also provided in Table 2 below.

TABLE 2

| Time | Statistic | Compound 1 (n = 9) | Placebo (n = 8) | Mean Difference | P-value (2-sample t-test) |
|---|---|---|---|---|---|
| Baseline | Mean | 191 | 168 | 23 | 0.4 |
| Day 14 | LSMean change | −1.9 | −38.2 | 36.3 | 0.04 |
| Day 21 (primary) | LSMean change | 31.5 | 0.2 | 31.3 | 0.048 |
| Day 29 | LSMean change | 32.5 | 13.1 | 19.4 | 0.2 |

The data set provided in Table 2 and depicted in FIG. 2 was created from the data set provided in Table 3. Table 3 includes the raw values of maximum muscle strength on the knee extension (KE) as measured in pounds (lbs) in the repeated measures knee extension strength test. The values in this data set reflect no calculation, imputation, or derivation of any kind. D1 is day 1 (baseline, pre-dose), D14 is day 14 (day when brace is removed), D21 is day 21 (primary endpoint for the study), and D29 is day 29, which is the final assessment during the treatment period. D42 is day 42, which is a safety, follow-up assessment, which was not intended for statistical analysis.

TABLE 3

| Subject | Group | Day 1 (Lbs) | Day 14 (Lbs) | Day 21 (Lbs) | Day 29 (Lbs) | Day 42 (Lbs) |
|---|---|---|---|---|---|---|
| A | Treated | 123 | 120.5 | 213 | 213 | 238 |
| B | Treated | 260.5 | 225.5 | 270.5 | 270.5 | 270.5 |
| C | Treated | 168 | 158 | 158 | 150.5 | 158 |
| D | Treated | 163 | 185.5 | 183 | 183 | 183 |
| E | Treated | 160.5 | 170.5 | 205.5 | 230.5 | 220.5 |
| F | Treated | 220.5 | 200.5 | 270.5 | 270.5 | 270.5 |
| G | Treated | 145.5 | 195 | | | |
| H | Treated | 215.5 | 163 | 225.5 | 235.5 | 265.5 |
| I | Treated | 265.5 | 255.5 | 270.5 | 225.5 | 270.5 |
| J | Placebo | 120.5 | 70.5 | 108 | 183 | 170.5 |
| K | Placebo | 270.5 | 233 | 258 | 270.5 | 265.5 |
| L | Placebo | 133 | 73 | 180.5 | 188 | 270.5 |
| M | Placebo | 215.5 | 100.5 | 205.5 | 220.5 | 240.5 |
| N | Placebo | 178 | 170.5 | 145.5 | 158 | 163 |
| O | Placebo | 110.5 | 108 | 110.5 | 110.5 | 113 |
| P | Placebo | 158 | 145.5 | 160.5 | 155.5 | 165.5 |
| Q | Placebo | 158 | 168 | 203 | | 195 |

Compound 1 was effective in reducing muscle atrophy during immobilization (i.e., reducing the rate of loss of muscle strength during immobilization relative to control subjects that received placebo) and for reducing atrophy following immobilization (i.e., increasing the rate of return of muscle strength to baseline following immobilization relative to control subjects that received placebo).

It was unexpected that a PPARδ agonist would be associated with preventing muscle atrophy (i.e., reducing the rate of loss of muscle strength during immobilization relative to control subjects that received placebo). Analysis showed that in subjects treated with Compound 1, measures of muscle atrophy that would be expected did not occur or could not be measured. In other words, there was a significant reduction in the rate of loss of muscle strength during immobilization in subjects that received Compound 1 relative to control subjects that received placebo. Further, the rate of loss of muscle strength during immobilization in subjects that received Compound 1 was reduced to almost zero, since subjects that received Compound 1 did not show a significant loss of muscle strength compared to their baseline measurements. Analysis also showed that mean change from baseline to day 21 in muscle strength for the group treated with Compound 1 showed superiority relative to control subjects that received placebo. By 14 days following the end of immobilization (i.e., day 28), change in muscle strength compared to baseline was no longer significantly different between the group treated with Compound 1 relative to control subjects that received placebo.

We claim:

1. A method of treating muscle atrophy in a subject comprising administering to the subject in need thereof (E)-[4-[3-(4-fluorophenyl)-3-[4-[3-(morpholin-4-yl)propynyl]phenyl]allyloxy]-2-methyl-phenoxy]acetic acid, or a pharmaceutically acceptable salt thereof.

2. The method of claim 1, wherein (E)-[4-[3-(4-fluorophenyl)-3-[4-[3-(morpholin-4-yl)propynyl]phenyl]allyloxy]-2-methyl-phenoxy]acetic acid, or a pharmaceutically acceptable salt thereof:
   increases muscle mass in the subject;
   modulates muscle growth, enhances muscle formation, increases muscle strength, maintains muscle strength or reduces loss of muscle strength in the subject; or
   reduces the rate of decrease in mitochondrial biogenesis in a muscle tissue; or
   combination thereof.

3. A method of modulating muscle in a subject with muscle atrophy comprising administering to the subject in need thereof (E)-[4-[3-(4-fluorophenyl)-3-[4-[3-(morpholin-4-yl)propynyl]phenyl]allyloxy]-2-methyl-phenoxy]acetic acid, or a pharmaceutically acceptable salt thereof,
   wherein the muscle modulation is selected from:
   increasing muscle mass in the subject;
   modulating muscle growth, enhancing muscle formation, increasing muscle strength, maintaining muscle strength or reducing loss of muscle strength in the subject; or
   reducing the rate of decrease in mitochondrial biogenesis in a muscle tissue; or combination thereof.

4. The method of claim 1, wherein (E)-[4-[3-(4-fluorophenyl)-3-[4-[3-(morpholin-4-yl)propynyl]phenyl]allyloxy]-2-methyl-phenoxy]acetic acid, or a pharmaceutically acceptable salt thereof,
   reduces the rate of loss of Type I muscle fibers.

5. The method of claim 1, wherein:
   the treatment comprises activating PPARδ in skeletal muscle in the subject.

6. The method of claim 5, wherein:
   the muscle atrophy is skeletal muscle atrophy secondary to a chronic disease.

7. The method of claim 6, wherein:
   the chronic disease is a neurologic disease or drug-induced muscle disease.

8. The method of claim 6, wherein:
   the chronic disease is multiple sclerosis, amyotrophic lateral sclerosis, spinal muscular atrophy, critical illness neuropathy, cancer, congestive heart failure, chronic pulmonary disease, chronic renal failure, chronic liver disease, diabetes mellitus, Cushing syndrome, chronic infection, glucorticoid-induced myopathy, statin-induced myopathy, polymyositis or dermatomyositis.

9. The method of claim 1, wherein:
   the muscle atrophy is skeletal muscle atrophy secondary to a genetic disease that primarily affect skeletal muscle.

10. The method of claim 9, wherein:
    the genetic disease is muscular dystrophy or myotonic dystrophy.

11. The method of claim 1, wherein:
    (E)-[4-[3-(4-Fluorophenyl)-3-[4-[3-(morpholin-4-yl)propynyl]phenyl]allyloxy]-2-methyl-phenoxy]acedic acid, or a pharmaceutically acceptable salt thereof, is administered at a dose of 50-200 mg per day.

* * * * *